(12) United States Patent
Zayed et al.

(10) Patent No.: US 11,304,832 B2
(45) Date of Patent: Apr. 19, 2022

(54) FENESTRATED STENT SYSTEM AND METHOD OF USE

(71) Applicants: Mohamed Zayed, St. Louis, MO (US); Alexander J. Wirtz, St. Louis, MO (US)

(72) Inventors: Mohamed Zayed, St. Louis, MO (US); Alexander J. Wirtz, St. Louis, MO (US)

(73) Assignee: Washington University, St. Louis, MO (US)

( * ) Notice: Subject to any disclaimer, the term of this patent is extended or adjusted under 35 U.S.C. 154(b) by 101 days.

(21) Appl. No.: 16/392,283

(22) Filed: Apr. 23, 2019

(65) Prior Publication Data

US 2019/0321203 A1    Oct. 24, 2019

Related U.S. Application Data

(60) Provisional application No. 62/661,398, filed on Apr. 23, 2018.

(51) Int. Cl.
| | |
|---|---|
| *A61F 2/07* | (2013.01) |
| *A61F 2/86* | (2013.01) |
| *A61F 2/82* | (2013.01) |
| *A61F 2/06* | (2013.01) |

(52) U.S. Cl.
CPC .............. *A61F 2/86* (2013.01); *A61F 2/07* (2013.01); *A61F 2002/065* (2013.01); *A61F 2002/821* (2013.01); *A61F 2230/0069* (2013.01)

(58) Field of Classification Search
CPC .............. A61F 2/92; A61F 2250/0039; A61F 2002/065

USPC ............................... 623/1.36–1.48
See application file for complete search history.

(56) References Cited

U.S. PATENT DOCUMENTS

| | | | | |
|---|---|---|---|---|
| 5,902,334 | A * | 5/1999 | Dwyer | A61F 2/95 606/194 |
| 8,795,349 | B2 * | 8/2014 | Huser | A61F 2/07 623/1.13 |
| 8,870,939 | B2 * | 10/2014 | Roeder | A61F 2/07 623/1.13 |
| 9,095,461 | B2 | 8/2015 | Schaeffer | |
| 9,168,160 | B2 * | 10/2015 | Jensen | A61F 2/07 |
| 9,517,124 | B2 | 12/2016 | Sithian | |
| 10,588,735 | B2 * | 3/2020 | Dake | A61F 2/07 |
| 2005/0165480 | A1 * | 7/2005 | Jordan | A61B 17/12181 623/9 |
| 2006/0095118 | A1 | 5/2006 | Hartley | |
| 2009/0157164 | A1 * | 6/2009 | McKinsey | A61F 2/07 623/1.13 |
| 2011/0257731 | A1 * | 10/2011 | Hartley | A61F 2/856 623/1.35 |
| 2012/0130478 | A1 * | 5/2012 | Shaw | A61F 2/07 623/1.35 |
| 2012/0323303 | A1 * | 12/2012 | Ivancev | A61F 2/07 623/1.13 |

(Continued)

*Primary Examiner* — Suzette J Gherbi
(74) *Attorney, Agent, or Firm* — Polsinelli, PC

(57) ABSTRACT

The disclosure provides for a device and method for treating aortoiliac occlusion disease with the placement of a fenestrated stent system at the aortic bifurcation. The fenestrated stent system includes a tapered fenestrated stent with a fenestration and a common iliac stent that is placed within the fenestration of the fenestrated stent.

17 Claims, 40 Drawing Sheets
(30 of 40 Drawing Sheet(s) Filed in Color)

(56) References Cited

U.S. PATENT DOCUMENTS

| | | | | |
|---|---|---|---|---|
| 2013/0116773 A1* | 5/2013 | Roeder | ............... | A61F 2/07 623/1.15 |
| 2015/0073534 A1* | 3/2015 | Roeder | ............... | A61F 2/07 623/1.35 |
| 2015/0265441 A1* | 9/2015 | Weber | ............... | A61F 2/89 623/1.16 |
| 2016/0184078 A1* | 6/2016 | Choubey | ............... | A61F 2/07 623/1.13 |
| 2016/0184115 A1* | 6/2016 | Ondersma | ............... | A61F 2/86 623/1.35 |
| 2019/0192273 A1* | 6/2019 | Debus | ............... | A61F 2/064 |
| 2020/0268365 A1* | 8/2020 | Hebert | ............... | A61B 17/12031 |
| 2020/0268501 A1* | 8/2020 | Palermo | ............... | A61F 2/97 |
| 2020/0289255 A1* | 9/2020 | Perkins | ............... | A61F 2/07 |
| 2021/0052364 A1* | 2/2021 | Guo | ............... | A61F 2/07 |

\* cited by examiner

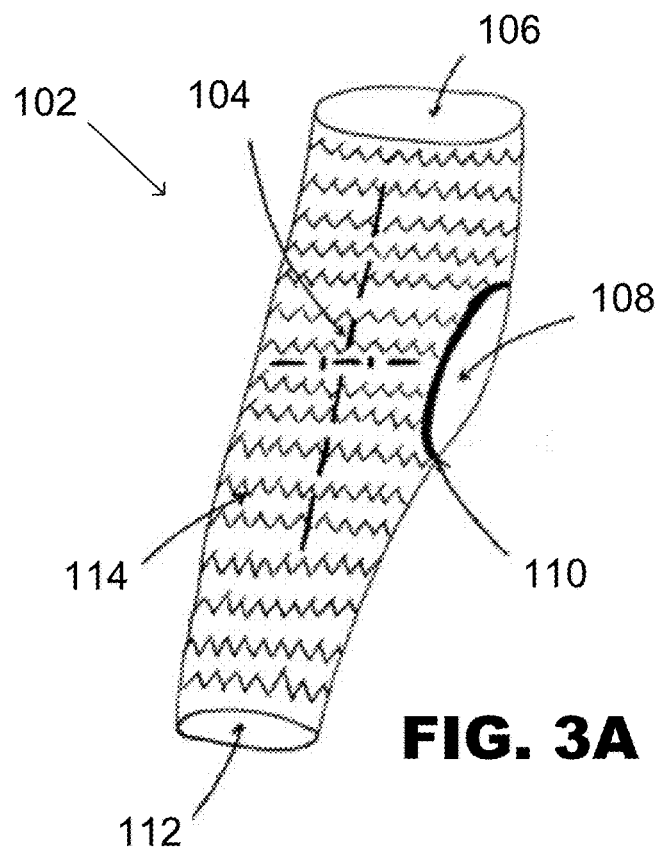
FIG. 3A
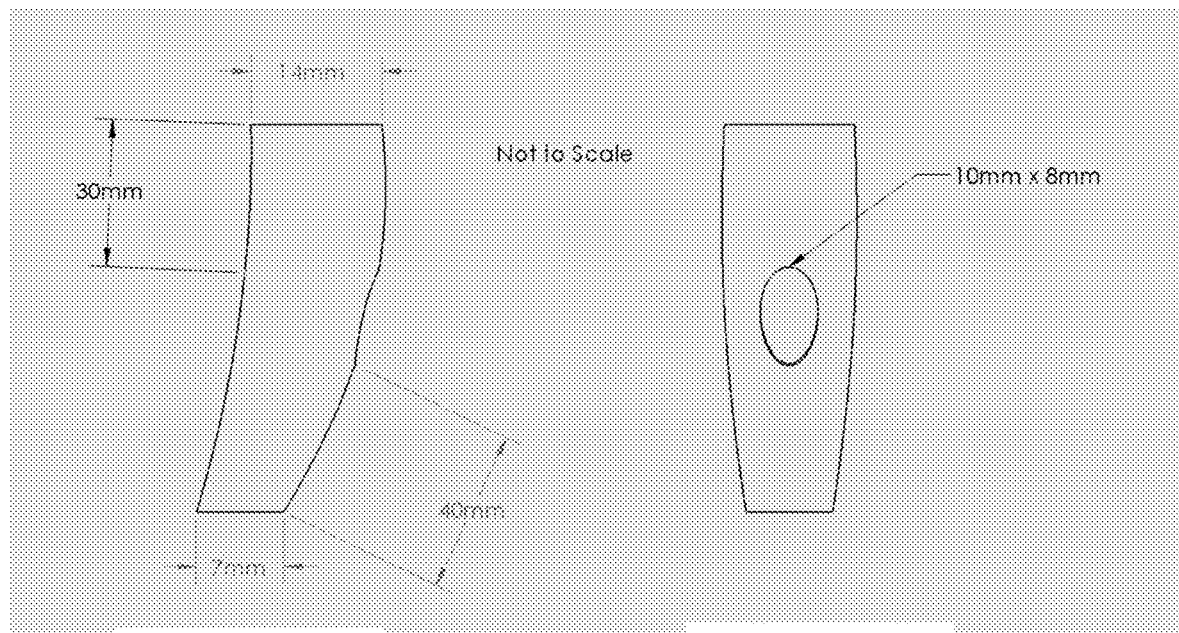
FIG. 3B  FIG. 3C

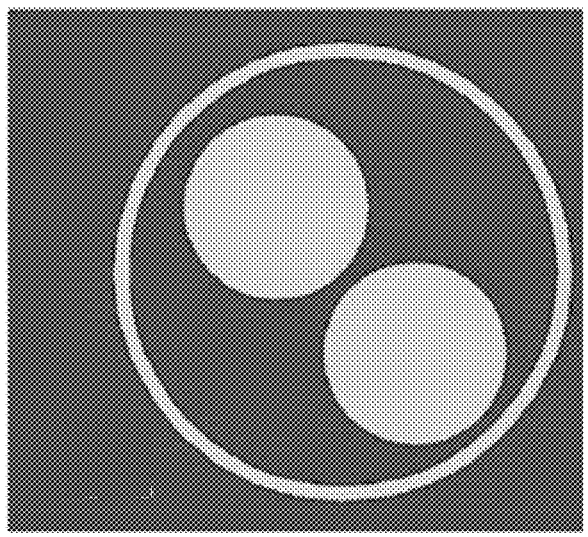 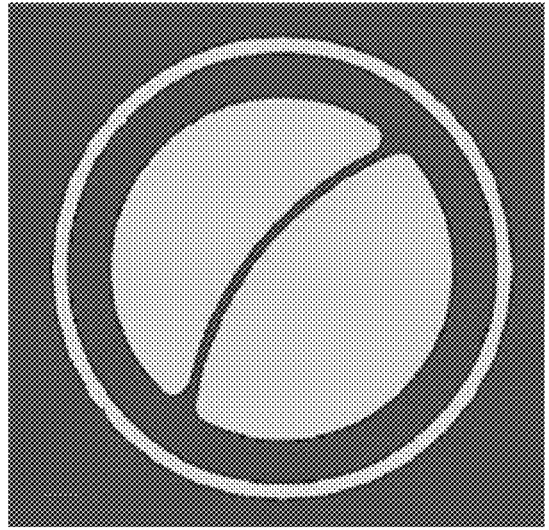
FIG. 17A  FIG. 17B
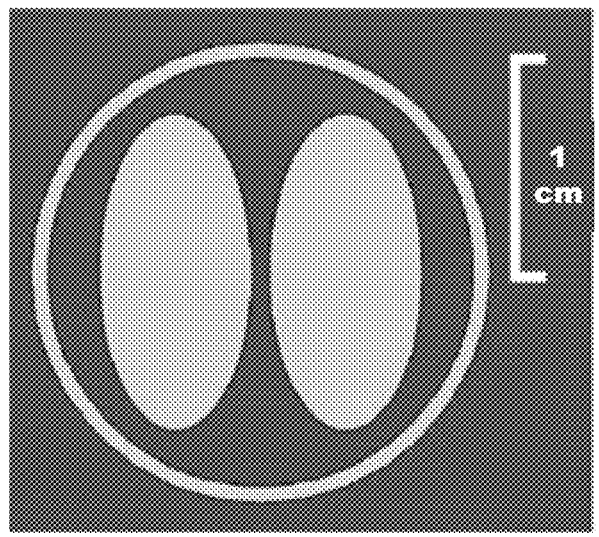
FIG. 17C

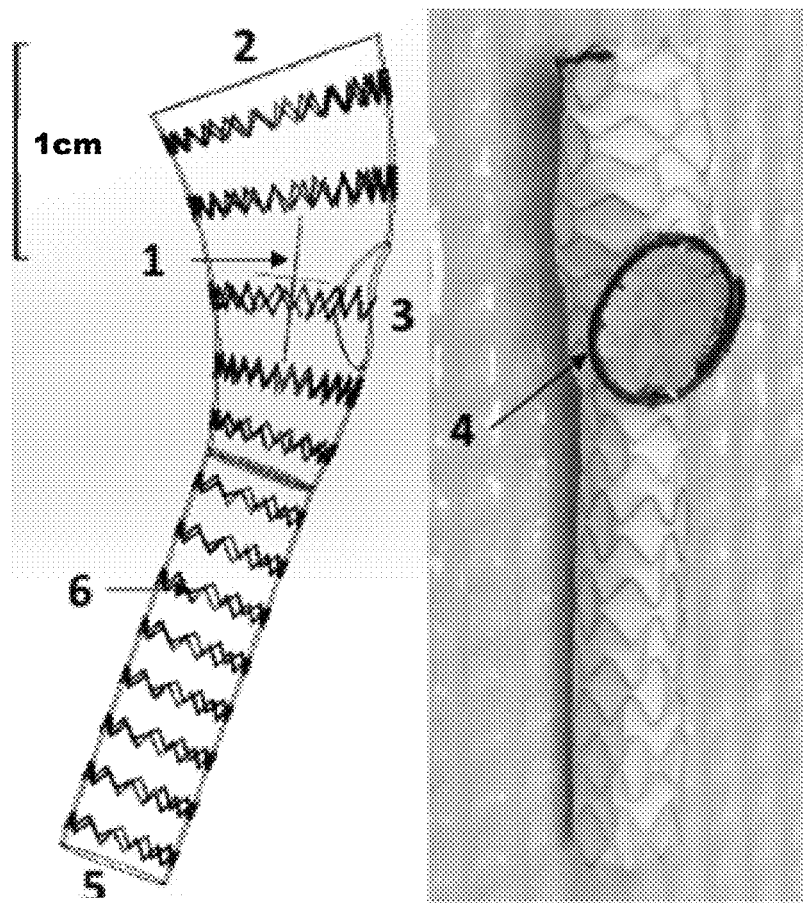
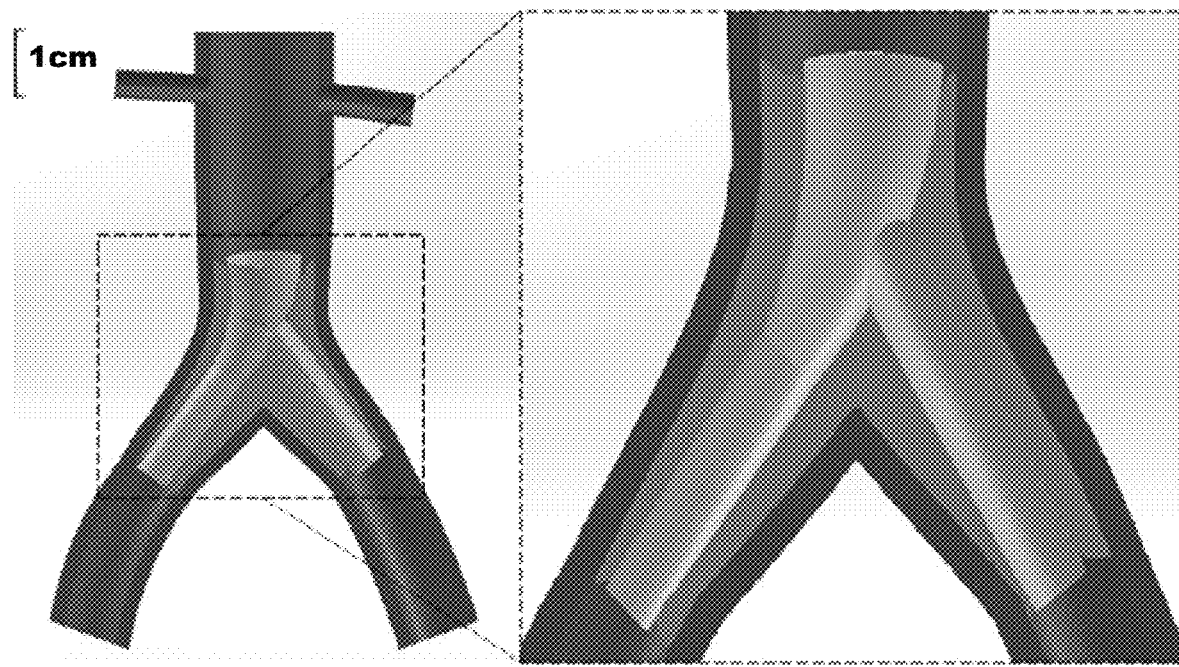
FIG. 18A  FIG. 18B
FIG. 18C  FIG. 18D

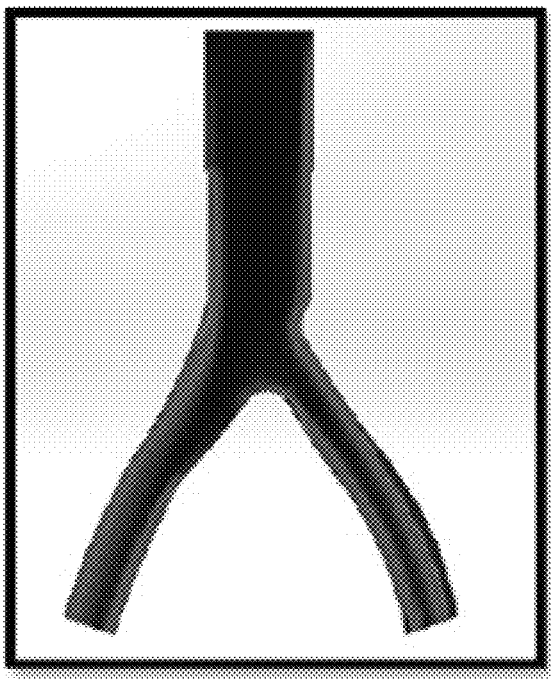 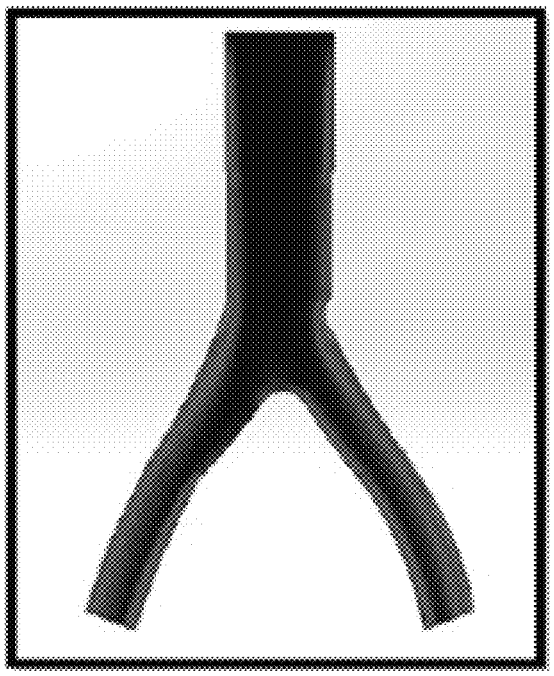
FIG. 19E  FIG. 19F

FENESTRATED STENT SYSTEM AND METHOD OF USE

CROSS REFERENCE TO RELATED APPLICATIONS

This application claims priority to U.S. Provisional Application No. 62/661,398, filed Apr. 23, 2018, the contents of which are entirely incorporated by reference herein.

FIELD

The present disclosure is directed to a fenestrated stent system for treatment of aortoiliac occlusive disease.

BACKGROUND

Aortoiliac occlusive disease is a result of atherosclerotic plaque accumulation in the lumen of the distal abdominal aorta and proximal common iliac arteries. Unimpeded blood flow in the aorto-iliac segment is essential to provide pelvic arterial perfusion, and arterial inflow to the bilateral lower extremities. Chronic progressive accumulation of atherosclerotic plaque in the distal aorta and common iliac arteries can cause a critical reduction in the blood flow to the lower extremities and pelvic organs such as the rectum, gonads, and perineum. Complete occlusion of the aorto-iliac arterial segment can lead to significant lower extremity ischemia with high morbidity, disability, wounds/ulcerations, and elevated risk of amputation. It is important to identify patients who are at risk of progressive aorto-iliac occlusive disease, and to provide them with durable treatments that can restore luminal patency.

It is hypothesized that aorto-iliac occlusive disease commonly results from chronic turbulence at the aortic bifurcation, which leads to plaque deposition and buildup over time. Schematic representation of healthy and occluded aortic bifurcations may be seen in FIG. 15A and FIG. 15B. Individuals with risk factors such as advanced age, smoking, diabetes, hyperlipidemia, and/or hypertension are more likely to develop more progressive plaque accumulation in this bifurcation region as well as other arterial tree bifurcations such as the carotid artery bifurcation, renal artery origins, and mesenteric artery origins. It is estimated that 25 percent of the United States population over the age of 70 has evidence of aorto-iliac occlusive disease, with an estimated overall prevalence of 8.5 million people affected overall. However, this is likely an underestimation since approximately half of all individuals with aorto-iliac occlusive disease do not exhibit any apparent symptoms prior to the onset of critical ischemic symptoms in the lower extremities and/or pelvis.

There are two commonly used methods for the treatment of symptomatic aorto-iliac disease. One method is open bypass surgery that serves to divert blood flow from a non-diseased proximal segment of the aorta to a relatively non-diseased distal segment of the iliac and/or femoral arteries (at the groin level). Open surgical bypass can be associated with elevated risks in patients with advanced age and other cardiovascular morbidities. Therefore, a less invasive, commonly used alternative to open bypass is the endovascular recanalization and stenting of the aorto-iliac arterial segment. Given the inverse Y shaped configuration of this arterial segment, it is often approached from bilateral femoral artery cannulation and delivery of stents to the aorto-iliac segment in a retrograde fashion. Stents used for this treatment are typically balloon expandable stents and are commonly stents that are covered with PTFE (polytetrafluoroethylene) lining. The stents are also often deployed directly adjacent to one another (kissing stent configuration) in order to provide flow from the aorta to the bilateral iliac artery systems. A schematic of this can be seen in FIG. 15C. This approach has been found to be useful in restoring blood flow through the diseased aorto-iliac system using stents that can be expanded to a particular diameter using intraluminal balloons, reduce the risk of extraluminal bleeding given their covered nature.

Despite the common practice of kissing stent deployment there are currently no balloon-expandable stents that are actually approved by the Food and Drug Administration for this use. Therefore, all kissing stent procedures are currently performed outside the instructions of use for these devices and their long-term patency has not been evaluated by a regulatory body.

A significant portion, if not all, discrepancies from the kissing stent procedure stem from the inlet of the two stents in the distal aorta. As these two iliac stents are designed to operate separately in the common iliac arteries, the procedure places the stents outside of their design parameters in attempting to have them interface with each other within the distal aorta. In clinical practice, variability is commonly noted at the inlet of these kissing stents, with one stent occluding the other along their length. A representative MRI example of this may be seen in FIG. 16.

The optimal placement of these stents in a manner which poses the least risk to the patient is dependent upon the best judgement of the operator, and commonly applied examples are illustrated in FIG. 17A, FIG. 17B and FIG. 17C.

FIG. 17A represents a situation where arterial pressure is a key concern. As the operator seeks to avoid rupturing the distal aorta post-deployment, the stents are not fully expanded to the inner diameter of the distal aorta. This results in two smaller stent openings diverting blood flow to the two common iliac arteries. This approach presents several issues, chiefly among them being that as the stents have not decompressed to fill the maximum diameter of the vessel, the flow of blood to the lower extremities is inhibited. Consequentially, blood will flow around these stents into various gaps in the plaque as the area surrounding the two kissing stent inlets is not impermeable. This increases the risk of stent thrombosis and recurrence of symptoms. Another significant issue in this approach is that the stents may deploy in an offset manner, resulting in an asymmetric inlet which may lead to an increase in fluid flux in the stents. The vorticity of the blood spiraling through each iliac stent is consequently increased prior to its reaching the iliac arteries, resulting in the potential for flow stagnation and the further increased risk of thrombosis.

FIG. 17B represents the complete decompression of the stents during deployment. As these stents are not designed to support non-radial forces however, the outward pressure from one stent commonly results in one becoming concave and the other convex. This introduces more significant issues to the patient, as the amount of residual stress present at this inlet may lead to a rupture of the distal aorta. This concentration of stress may also cause one or both stents to kink, resulting in the blockage of blood flow to lower extremities as observed in FIG. 16. Additionally, a similar issue with vorticity will occur, as the stents are more asymmetrical at the inlet than in case A due to each stent presenting a non-circular cross-section leading to heightened vorticity levels and the potential for thrombosis.

FIG. 17C is regarded as the theoretically optimal deployment of the kissing stents. Due to the design limitations of these stents however, it is noted to be practically impossible to attain in practice.

Accordingly, there remains a need in developing a fenestrated, minimally invasive balloon expandable stent for treatment of aortoiliac occlusive disease. These and other needs are provided in this disclosure.

BRIEF SUMMARY

The disclosure provides for a fenestrated stent system for placement in the aortic bifurcation. The fenestrated stent system may include a fenestrated stent having a distal aorta end and a common iliac end. The fenestrated stent may include a fenestration at a point between the distal aorta end and the common iliac end and at least one radiopaque marker. The fenestrated stent is tapered from the distal aorta end to the common iliac end.

In some embodiments, the fenestrated stent is about 8 cm in length. In an embodiment, the taper from the distal aorta end to the common iliac end is about 50%. For example, the distal aorta end may have a diameter of about 14 mm and the common iliac end may have a diameter of about 7 mm. In an embodiment, the fenestration includes a radiopaque wireframe on the fenestration border. In various embodiments, the fenestration has an oval, circular, or triangular shape. For example, the fenestration may be oval-shaped and have a size of about 10 mm by about 8 mm. In another example, the fenestration has a diameter of about 15 mm. The fenestrated stent is balloon expandable. The fenestrated stent system may further include a common iliac stent for placement through the fenestration of the fenestrated stent and in the contralateral common iliac artery. In an embodiment, the common iliac stent may be tapered.

The disclosure further provides for a method of treating aortoiliac occlusion disease. The method may include placing a fenestrated stent at a location in the aortic bifurcation, identifying the location of the fenestrated stent, adjusting the fenestrated stent such that the distal aorta end is in the aorta and the common iliac end is in a common iliac, identifying the location of the fenestration, adjusting the fenestrated stent so that the fenestration aligns with the contralateral common iliac, and expanding a balloon to expand the fenestrated stent.

In some embodiments, the fenestrated stent may be about 8 cm in length. In an embodiment, the taper from the distal aorta end to the common iliac end is about 50%. For example, the distal aorta end may have a diameter of about 14 mm and the common iliac end may have a diameter of about 7 mm. The fenestration may include a radiopaque wireframe on the fenestration border. In various embodiments, the fenestration may have an oval, circular, or triangular shape. For example, the fenestration may be oval-shaped and have a size of about 10 mm by about 8 mm. The method may further include placing a common iliac stent through the fenestration of the fenestrated stent and in the contralateral common iliac artery. In an embodiment, the common iliac stent is tapered.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The application file contains at least one drawing executed in color. Copies of this patent application publication with color drawing(s) will be provided by the Office upon request and payment of the necessary fee.

The description will be more fully understood with reference to the following figures and data graphs, which are presented as various embodiments of the disclosure and should not be construed as a complete recitation of the scope of the disclosure, wherein:

FIG. 3A is a schematic of the fenestrated stent design according to one embodiment.

FIG. 3B is an illustration of the fenestrated stent in one embodiment.

FIG. 3C is an illustration of the fenestrated stent in one embodiment.

FIG. 17A, FIG. 17B, FIG. 17C depict cross-sections of variably deployed kissing stents as seen from their aortic inlet. (FIG. 17A) Protocol when arterial integrity is at risk due to arterial pressure concerns. (FIG. 17B) Typical stent configuration when stents are fully deployed. (FIG. 17C) Theoretically optimal positioning of stents, practically impossible to achieve in practice.

FIG. 18A, FIG. 18B, FIG. 18C, FIG. 18D depict computer generated and benchtop models of the proposed AIFEN stent. (FIG. 18A, FIG. 18B) Computer generated and physical prototype of the ipsilateral main body aortoiliac stent with features labeled as follows: (1) radiolucent "targeting" lines oriented perpendicular to one another on opposite sides of the stent, such that the operator may be assured of proper stent orientation upon deployment. (2) The aorta inlet. (3) The opening to accept the contralateral complementary iliac stent. (4) Radiolucent lining surrounding the opening for the contralateral complementary iliac stent to work in tandem with the "targeting" lines in assisting the operator in proper stent deployment. (5) The ipsilateral iliac outlet. (6) Mesh wires commonly utilized in stent construction. (FIG. 18C, FIG. 18D) Computer generated cross-section of the AIFEN stent deployed within a plaque-occluded aortoiliac and its cutaway.

FIG. 19A, FIG. 19B, FIG. 19C, FIG. 19D, FIG. 19E, FIG. 19F depict vorticity maps of flow through the six models. (FIG. 19A) Healthy aortic bifurcation. (FIG. 19B) Unhealthy aortic bifurcation. (FIG. 19C) Ideally deployed "kissing" stents. (FIG. 19D) 5 mm OD fenestration AIFEN. (FIG. 19E) 10 mm OD fenestration AIFEN. (FIG. 19F) 15 mm OD fenestration AIFEN.

DETAILED DESCRIPTION

Figure 1:
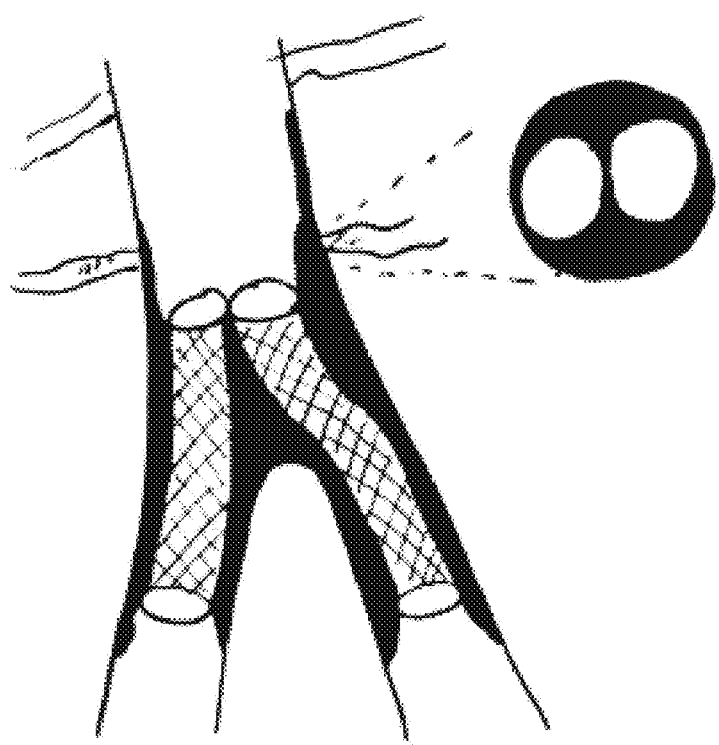
FIG. 1 is a schematic of the aortic bifurcation with placed kissing stents and observable cross-section.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, "substantially cylindrical" means that the object resembles a cylinder, but can have one or more deviations from a true cylinder. The terms "comprising," "including" and "having" are used interchangeably in this disclosure. The terms "comprising," "including" and "having" mean to include, but not necessarily be limited to the things so described.

The fenestrated stent system described herein is constructed to overcome the major disadvantages involved in treating aortoiliac occlusive disease and overcomes some of the issues with the current state of the art for treating aortoiliac occlusion disease, including kissing arterial stents. The kissing arterial stenting procedure, while commonly used in practice, has major disadvantages in the design. Kissing stent patency has been shown to be very good in initial years, but degrade over time. However, it is still praised as the best solution to aortoiliac occlusive disease as no other solutions have a presence in medical practice today. When the initial common iliac stent is placed from a common iliac artery to the distal aorta, significant blood flow is redirected to that initial common iliac artery, depriving the other contralateral common iliac of needed blood flow. A solution to this major issue is to introduce a blood bypass from the distal aorta to the common iliac arteries, but this causes the procedure to be much more invasive for the patient. In FIG. 1, the schematic shows the available inlet cross-section of the kissing stents, which only occupies approximately 50-60% of the distal aorta area at the inlet. The rest of the distal aorta area may be occupied by compressed plaque, as seen in FIG. 1, or there may be significant gaps that allows stagnate blood flow to flow in, become trapped, and form a thrombus which increases the risk of embolization post-procedure. Two kissing stents may also introduce a large amount of stress on the distal aorta due to their unintentional use in the vessel. Introducing a stent in a vessel already presents a certain amount of residual stress on the vessel itself, so two maximally dilated stents in this space can cause an internal failure issue for the distal aorta. The fenestrated stent system overcomes these numerous concerns and design issues.

Disclosed herein are fenestrated stent systems and methods for stenting the aortoiliac bifurcation for treatment of aortoiliac occlusive disease. For example, the fenestrated stent system may include a fenestrated stent with a fenestration or opening at a point along the length of the fenestrated stent and a secondary common iliac stent that fits within the fenestration of the fenestrated stent.

Figure 2:
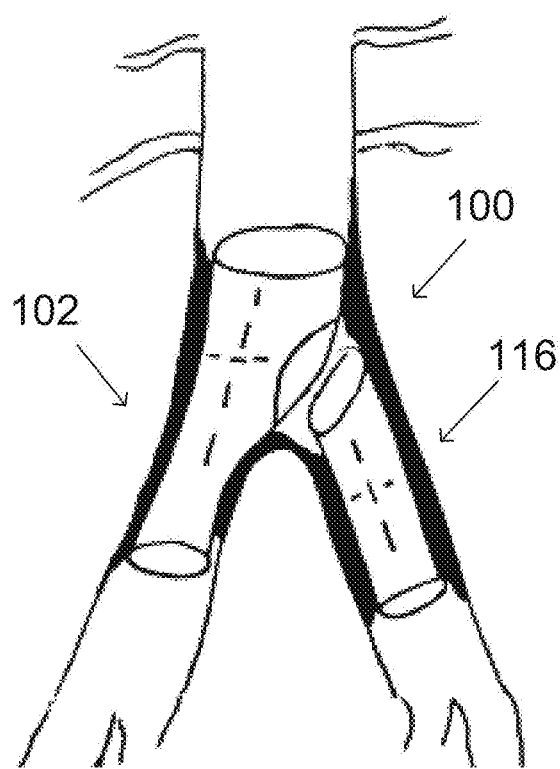
FIG. 2 is a schematic of the aortic bifurcation with the fenestrated stent design in the aortoiliac bifurcation in one embodiment.

The fenestrated stent is a balloon expandable tapered stent that includes a fenestration to allow antegrade blood flow to the contralateral common iliac artery immediately after deployment. The fenestrated stent is designed to act as a single, ordinary stent in the aortic bifurcation with a fenestration that will remove the need to perform a bypass on the patient during the angioplasty procedure. Additionally, a secondary common iliac stent can be placed in the contralateral common iliac artery in tandem with the fenestrated stent in order to treat the occlusive disease from the entire bifurcation. A schematic of this fenestrated stent system can be seen in FIG. 2.

The fenestrated stent will be placed in the distal aorta and one common iliac per the method of balloon angioplasty known in the art. Once the stent is positioned in the diseased vessel, a series of specifically placed radiopaque markers on the stent or catheter may allow the practitioner to arrange the stent such that the fenestration is facing the contralateral common iliac. The balloon will then expand to allow the stent to form to the inner walls of the vessel and crush the plaque to create a new lumen for blood flow and thus restoring patency. Due to the tapered design, the stent may fit more securely with the shape of the aortic bifurcation and will not produce any more residual stress than necessary. The positioning of the fenestration may allow antegrade blood flow to immediately resume to the lower extremities on both sides of the patient and thus removing any need for an invasive blood bypass. Then, a second, similar procedure can be done to place the secondary common iliac stent in the contralateral iliac artery to completely treat the aortic bifurcation for occlusive disease.

Using models of the healthy and unhealthy aortic bifurcation to establish a fundamental range of acceptable values and outcomes, the Examples below show that the fenestrated stent system provides an improvement over the kissing stents angioplasty method. With computer-aided design models and a fluid simulation of non-Newtonian blood pulsating flow, the fenestrated stent system may provide improved treatment options for aortoiliac occlusive disease. The most significant evidence of superiority of the fenestrated stent system and method of use is in the velocity contour plots and velocity vector maps of each aortic bifurcation simulation in the Examples below. Substantial issues such as stagnation, high velocities, and back-flow are involved in the common kissing stent angioplasty technique, and these issues are eliminated in the fenestrated stent system. The fenestrated stent may provide a smooth transition of blood flow in the bifurcation from the distal aorta to the common iliac arteries. Provided that pressure is maintained throughout the aortic bifurcation model, the fenestrated stent system demonstrates a reduction in peak average velocity as compared to the kissing arterial stenting procedure. Therefore, the fenestrated stent system used in the aortic bifurcation may provide superior performance in treating aortoiliac occlusive disease.

Fenestrated Stent

The fenestrated stent system 100 may include a tapered fenestrated stent 102. An image of the fenestrated stent in one embodiment can be seen in FIG. 4. As illustrated in FIG. 3A, the fenestrated stent 102 may include a distal aorta end 106 and a common iliac end 112. In an embodiment, the fenestrated stent 102 is tapered from the distal aorta end 106 to the common iliac end 112. The fenestrated stent may have a similar length and diameter of an arterial stent, except that the diameter tapers from a larger diameter at the distal aorta end and a smaller diameter at the common iliac end. This allows for the fenestrated stent to more closely match the size of the aorta and common iliac artery, respectively. In one embodiment, the diameter of the fenestrated stent may decrease by about 45% to about 95% from the distal aorta end to the common iliac end. In various embodiments, the amount of the taper from the distal aorta end to the common iliac end may be about 45%, about 50%, about 55%, about 60%, about 65%, about 70%, about 75%, about 80%, about 85%, about 90%, or about 95%. The diameter of the fenestrated stent may range from about 5 mm to about 25 mm. In various aspects, the fenestrated stent may vary in diameter along its length. The fenestrated stent may have a diameter of about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or about 25 mm at a point along the length of the fenestrated stent. In one aspect, as seen in FIG. 3B, the diameter of the fenestrated stent at the distal aorta end may be about 14 mm and the diameter of the fenestrated stent at the common iliac end may be about 7 mm. In another aspect, the diameter of the fenestrated stent at the distal aorta end may be about 20 mm and the diameter of the fenestrated stent at the common iliac end may be about 9 mm. The fenestrated stent may have a length of about 50 mm to about 150 mm. In various embodiments, the fenestrated stent has a length of about 50 mm to about 90 mm, from about 70 mm to about 110 mm, from about 90 mm to about 130 mm, and from about 110 mm to about 150 mm. In one embodiment, as seen in FIG. 3B, the fenestrated stent may have a length of about 80 mm.

The fenestrated stent may be made of any biocompatible materials capable of being utilized with a balloon expandable stent. In an embodiment, the fenestrated stent may have a wireframe mesh 114 over a cover. Non-limiting examples of the cover are Dacron and PTFE.

Figure 4A:
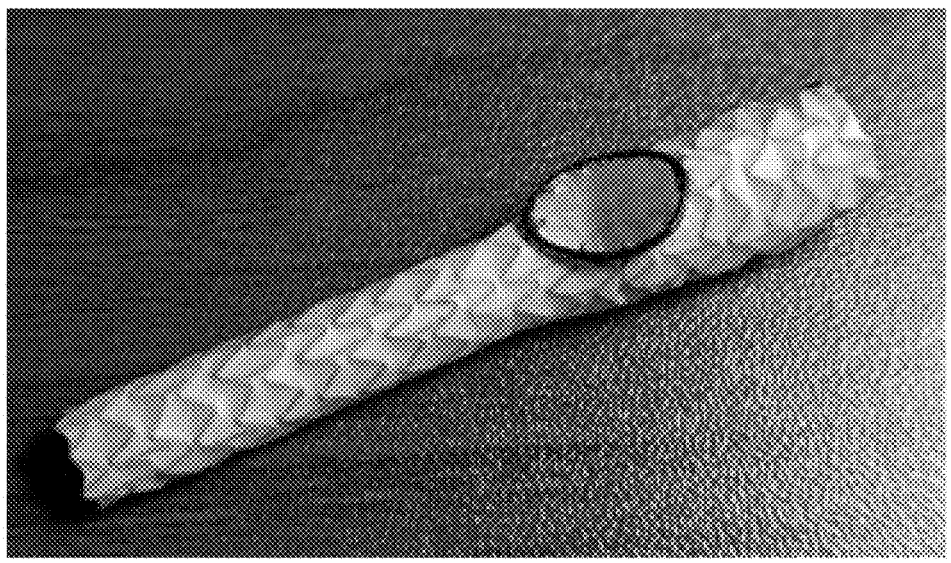
FIG. 4A is a photograph of a fenestrated stent in an embodiment.
Figure 4B:
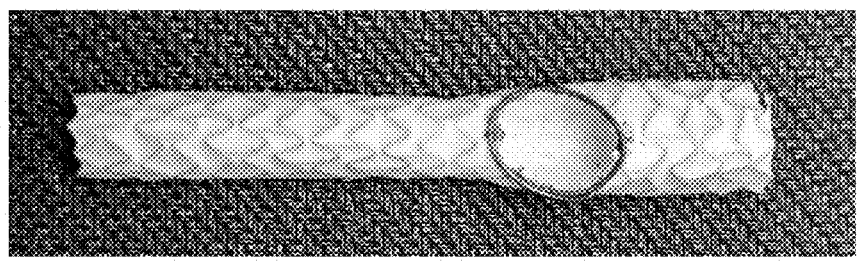
FIG. 4B is a photograph of a fenestrated stent in an embodiment.
Figure 4C:
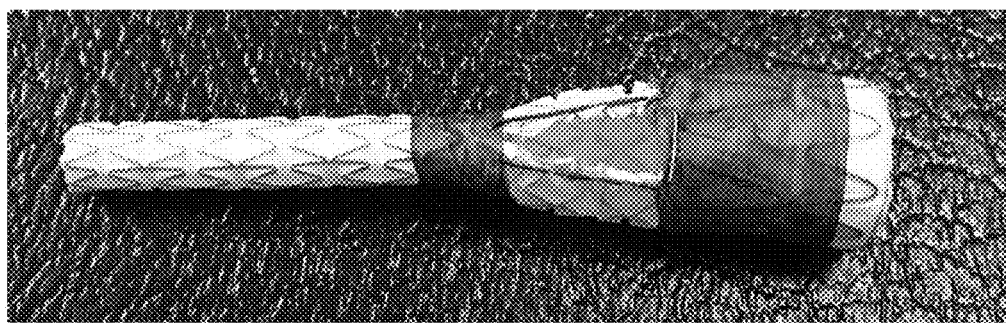
FIG. 4C is a photograph of a fenestrated stent in an embodiment.

The fenestrated stent 102 may include a fenestration or opening at a point between the distal aorta end 106 and the common iliac end 112. In an embodiment, as seen in FIG. 3B and FIG. 3C, the fenestration may located about halfway between the distal aorta end and the common iliac end. In other embodiments, as seen in FIG. 4A, FIG. 4B, and FIG. 4C, the fenestration may be located closer to the distal aorta end. In one embodiment, the fenestration may begin about 30 mm from the distal aorta end. The fenestration may be any size or shape that allows blood to flow to the contralateral common iliac. For example, the fenestration may be an oval, triangle, or circle. In one aspect, the fenestration may be an oval-shaped fenestration 108 for optimal blood flow to contralateral common iliac. The size of the fenestration may range from about 6 mm to about 25 mm. In various embodiments, the fenestration may have a diameter range of about 6 mm to about 20 mm, about 8 mm to about 20 mm, about 10 mm to about 20 mm, about 12 mm to about 20 mm, about 14 mm to about 20 mm, about 16 mm to about 20 mm, about 18 mm to about 22 mm, about 20 mm to about 25 mm, about 6 mm to about 15 mm, about 8 mm to about 15 mm, about 10 mm to about 15 mm, about 12 mm to about 15 mm, about 14 mm to about 15 mm, about 16 mm to about 18 mm, about 18 mm to about 20 mm, and about 15 mm to about 20 mm. In alternative embodiments, the fenestration may have a diameter of about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm.

In one embodiment, the fenestration may be an oval having a size of about 10 mm by about 8 mm. In another embodiment, the fenestration may have a diameter of about 15 mm.

The fenestration itself may be secured in the fenestrated stent with a metal wire for support. When the fenestration is in position with the contralateral common iliac artery, antegrade blood flow can immediately resume to the lower extremities on both sides of the patient. This removes any need for an invasive blood bypass.

The fenestration may allow a relatively evenly distributed mass blood flow from the distal aorta to both of the common iliac arteries. The fenestration may be optimized such that the blood flow can be directed evenly to both sides of the common iliac vessel from the distal aorta and less vorticity will be seen at the fenestration site.

In other embodiments, the fenestrated stent 102 may include at least one radiopaque positional marker 104. The radiopaque positional marker 104 may be located at any point on the fenestrated stent, including on the outer surface of the fenestrated stent or at the fenestration. In an embodiment, the radiopaque positional marker may be a single point, a line, crossing lines, or any marking that allows a practitioner to locate the position of the fenestrated stent. In some embodiments, the fenestrated stent 102 may also include a radiopaque wireframe 110 on the fenestration border. The radiopaque wireframe 110 may allow for a practitioner to locate the fenestration and position it over the contralateral common iliac artery.

Common Iliac Stent

In various aspects, the fenestrated stent system 100 further includes a common iliac stent 116. The common iliac stent 116 has a proximal end and a distal end. The common iliac stent 116 is designed to be inserted through the fenestration of the fenestrated stent 102 and into the contralateral common iliac.

The common iliac stent 116 may be made of similar materials as the fenestrated stent and may be deployed using balloon angioplasty.

In an embodiment, the proximal end of the common iliac stent 116 is retained within the fenestrated stent 102 at the fenestration while the remaining length of the common iliac stent to its distal end is in the contralateral common iliac. The diameter of the common iliac stent may range from about 10 mm to about 5 mm. In various embodiments, the common iliac stent is tapered from the proximal end to the distal end. For example, the common iliac stent may have a taper of about 5% to about 25%. This may allow the distal end of the common iliac stent to pass through the fenestration while retaining the proximal end of the common iliac stent within the fenestrated stent. The shape or extent of expansion of the common iliac stent may be optimized to the shape of the fenestration and the shape and size of the common iliac. For example, the common iliac stent may have a length of about 6 mm to about 15 mm.

In some embodiments, the common iliac stent may further include at least one radiopaque marker.

Methods of Using the Fenestrated Stent System

The fenestrated stent system may be used to treat aortoiliac occlusion disease by being placed at the aortic bifurcation. The fenestrated stent 102 is inserted by balloon angioplasty at the aortic bifurcation such that distal aorta end 106 is situated within the distal aorta and the common iliac end 112 of the fenestrated stent 102 is within a common iliac.

Once the fenestrated stent 102 is positioned in the diseased vessel, a series of radiopaque markers on the fenestrated stent 104 or on the catheter will allow the practitioner to arrange the stent such that the fenestration is facing the contralateral common iliac. When a balloon catheter has been guided to the diseased vessel, the practitioner inflates the balloon, allowing the stent to expand to the diameter of the vessel. In an embodiment, the fenestrated stent may be covered with a biocompatible plastic sheet that, with the wireframe mesh as support, compresses and crush most of the plaque to the outer edge of the vessel. This restores blood flow through the diseased artery as the stent becomes plastically deformed to support the vessel. Antegrade blood flow may then immediately resume to the lower extremities on both sides of the patient and thus remove a need for a bypass.

After the fenestrated stent 102 is in place, the common iliac stent 116 may be placed in the contralateral common iliac artery using a similar procedure as with the fenestrated stent.

The fenestrated stent system may be implanted to treat aortoiliac occlusive disease. In an embodiment, the fenestrated stent is placed alone to treat or reduce the effects of aortoiliac occlusive disease. Placing the common iliac stent in the contralateral iliac artery in addition to the fenestrated stent may completely treat the aortic bifurcation for occlusive disease.

EXAMPLES

Example 1: Device Introduction

The Aorto-Iliac Fenestrated (AIFEN) stent is a balloon-expandable tapered device which includes a fenestration to allow antegrade blood flow to the contralateral common iliac artery upon deployment. The inclusion of this fenestration allows a stent to be applied in the bridging of the aortic bifurcation without the need to perform a bypass on the patient during the angioplasty procedure due to antegrade blood flow to the contralateral common iliac artery being facilitated. This unique fenestrated stent will be referred to as the ipsilateral main body aortoiliac stent from this point on. This ipsilateral stent also allows for a secondary, contralateral complementary iliac stent to be placed in tandem with the ipsilateral main body stent to treat the occlusive disease for the entire bifurcation. This complementary stent may be placed into the fenestration and flared out by balloon angioplasty to establish a smooth, transitional path for the flow of blood through the bifurcation. A schematic of this design concept may be seen in FIG. 18A.

Once the AIFEN stent is positioned in the diseased vessel, a series of specifically placed radiopaque markers on the catheter may allow the practitioner to orient the stent such that the fenestration is facing the contralateral common iliac as seen labeled as (1) and (4) in FIG. 18A and FIG. 18B. The balloon may then be expanded to allow the stent to form to the inner walls of the vessel, crushing the plaque to create a new lumen for blood flow as seen in FIG. 18C and FIG. 18D. Due to the tapered design, the stent may more securely interface with the wall of the aortic bifurcation and will consequently avoid presenting additional residual stresses in the creation of a new lumen within the vessel. The contralateral common iliac artery allows for the resumption of antegrade blood flow to the lower extremities on both sides of the patient, at which point a second, similar procedure may be conducted to place the contralateral complementary stent into the contralateral iliac artery. This may be done by extending a small portion of the complementary iliac stent into the fenestration of the ipsilateral main body stent and flaring the stent with an angioplasty balloon, resulting in a completed structure illustrated in FIG. 18C and FIG. 18D.

Example 2: Study Overview

Disclosed herein is the analysis of the projected performance of the AIFEN stent in comparison to commonly utilized procedures in the treatment of aortoiliac occlusive disease. To that end, computational fluid dynamic (CFD) simulations were utilized in the analysis of blood flow and to determine tendency for flow stagnation. This allowed for the likelihood of blood clotting in the aortic bifurcation resulting from the application of both stenting procedures to be quantified. As minimally invasive surgery is desired for this treatment, the aortoiliac bypass or any other bypass-related solution was not considered in this analysis. Six models were analyzed: a healthy aortic bifurcation, an unhealthy aortic bifurcation, ideally deployed kissing stents, and three proposed AIFEN stent designs with 5, 10, and 15 mm OD openings respectively for the interface of the ipsilateral main body aortoiliac stent with the contralateral complementary iliac stent.

Although the theoretically optimal deployment of the kissing stents (FIG. 17C) is noted to be practically impossible to attain in practice, it will be assumed for the purposes of these Examples that the kissing stents are deployed in this manner, and the results will be compared to the proposed AIFEN stenting procedures.

Example 3: Models for the Aortic Bifurcation

Figure 5A:
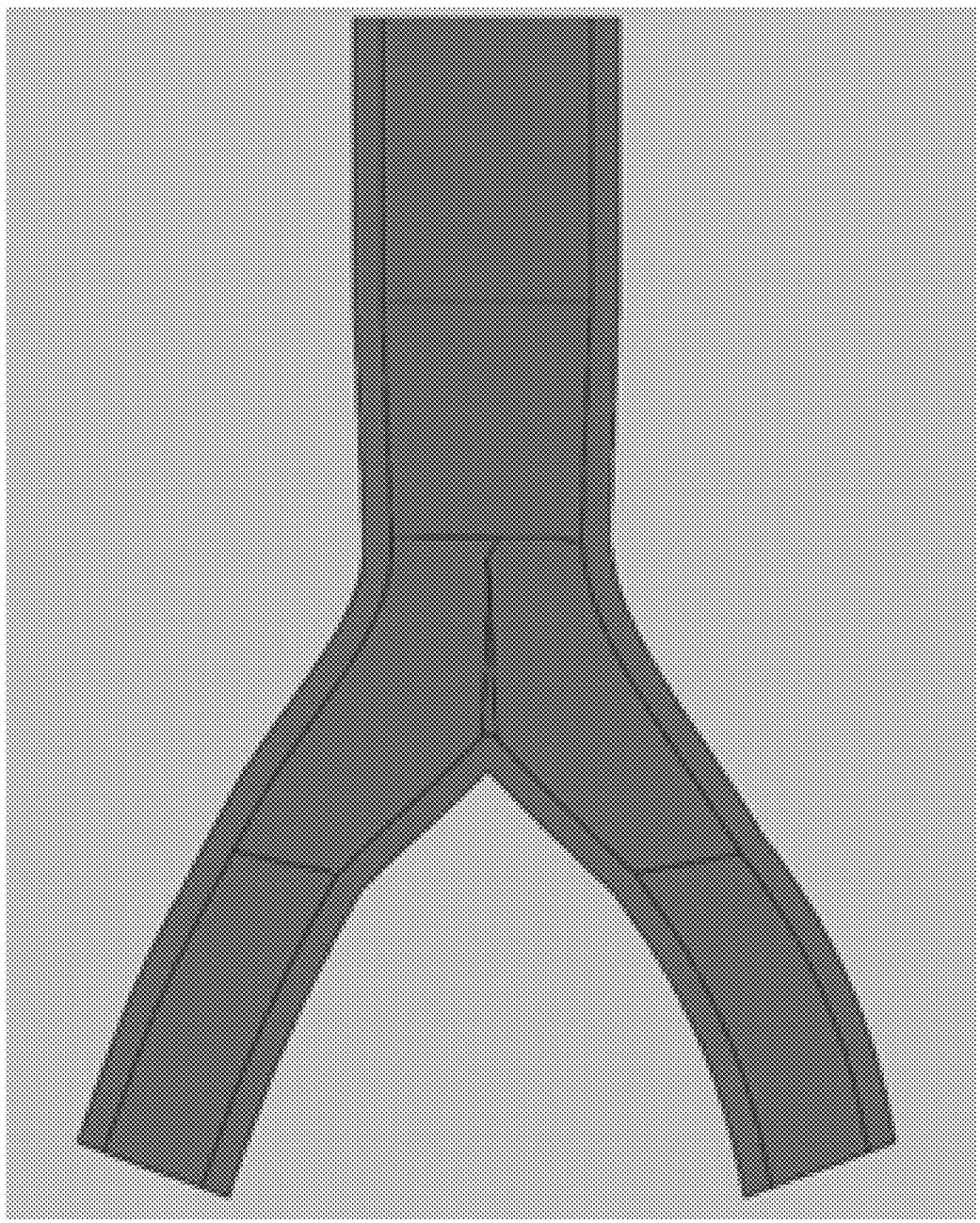
FIG. 5A is a cross-section of the healthy aortic bifurcation model.
Figure 5B:
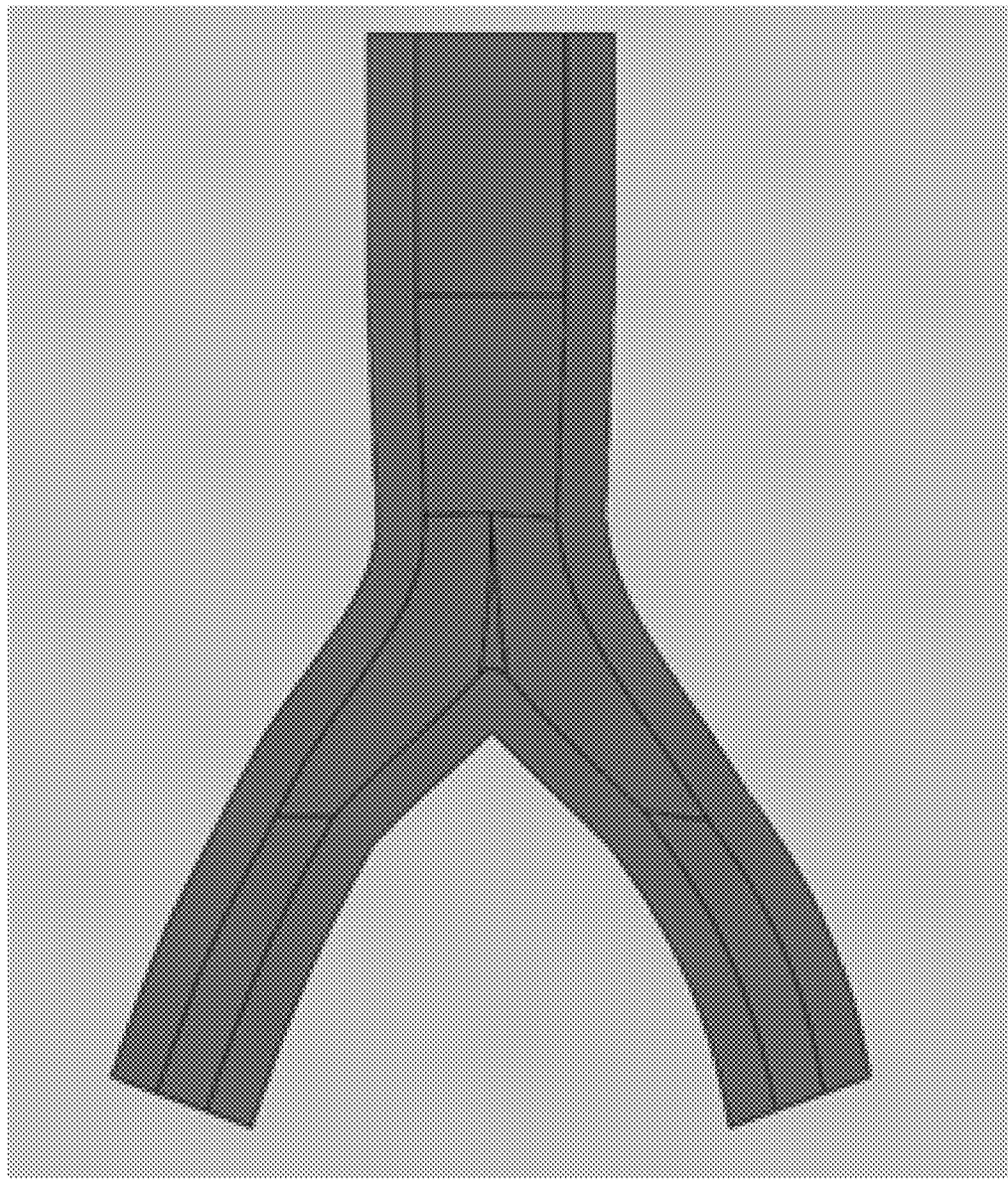
FIG. 5B is a cross-section of the unhealthy aortic bifurcation model.

Models of a healthy and unhealthy aortic bifurcation were developed to compare the performance of each stenting procedure in a routine and worst-case scenario. The healthy bifurcation was developed with a distal aorta inner diameter of 22 mm and a common iliac diameter of 12 mm. The bifurcation was created symmetrically with an angle of 25 degrees from the vertical. The length of the distal aorta present in the healthy model was 40 mm and the length of both common iliac arteries was 30 mm. The unhealthy bifurcation was developed with a distal aorta inner diameter of 12 mm and a common iliac diameter of 6 mm. This reflects clinical findings that aortoiliac occlusive disease routinely occludes vessels to such an extent that upon the onset of significant symptoms, the effective reduction in vessel diameter is 50 percent. The bifurcation reflects the healthy model, in that it was symmetrical with an angle of 25 degrees from the vertical. The length of the distal aorta present in the unhealthy model was 40 mm and the length of both iliac arteries is 30 mm. The cross-sections of these two CAD models can be seen in FIG. 5A and FIG. 5B.

Figure 6A:
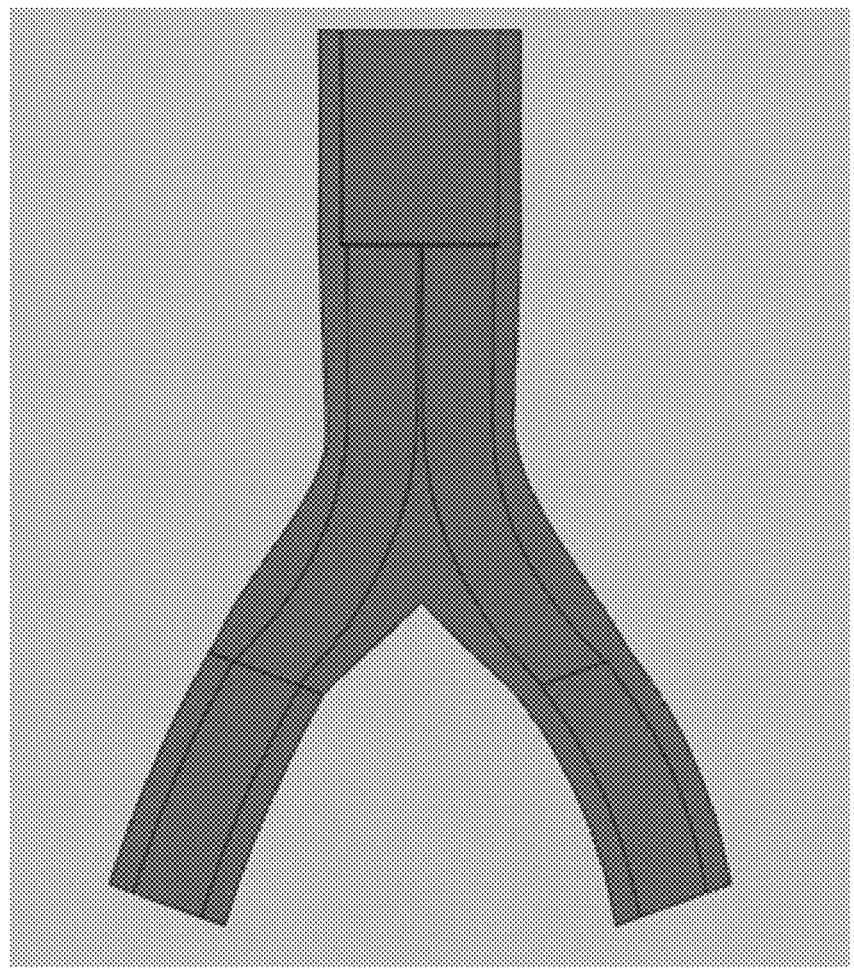
FIG. 6A is a cross-section of the aortic bifurcation model with placed kissing stents.
Figure 6B:
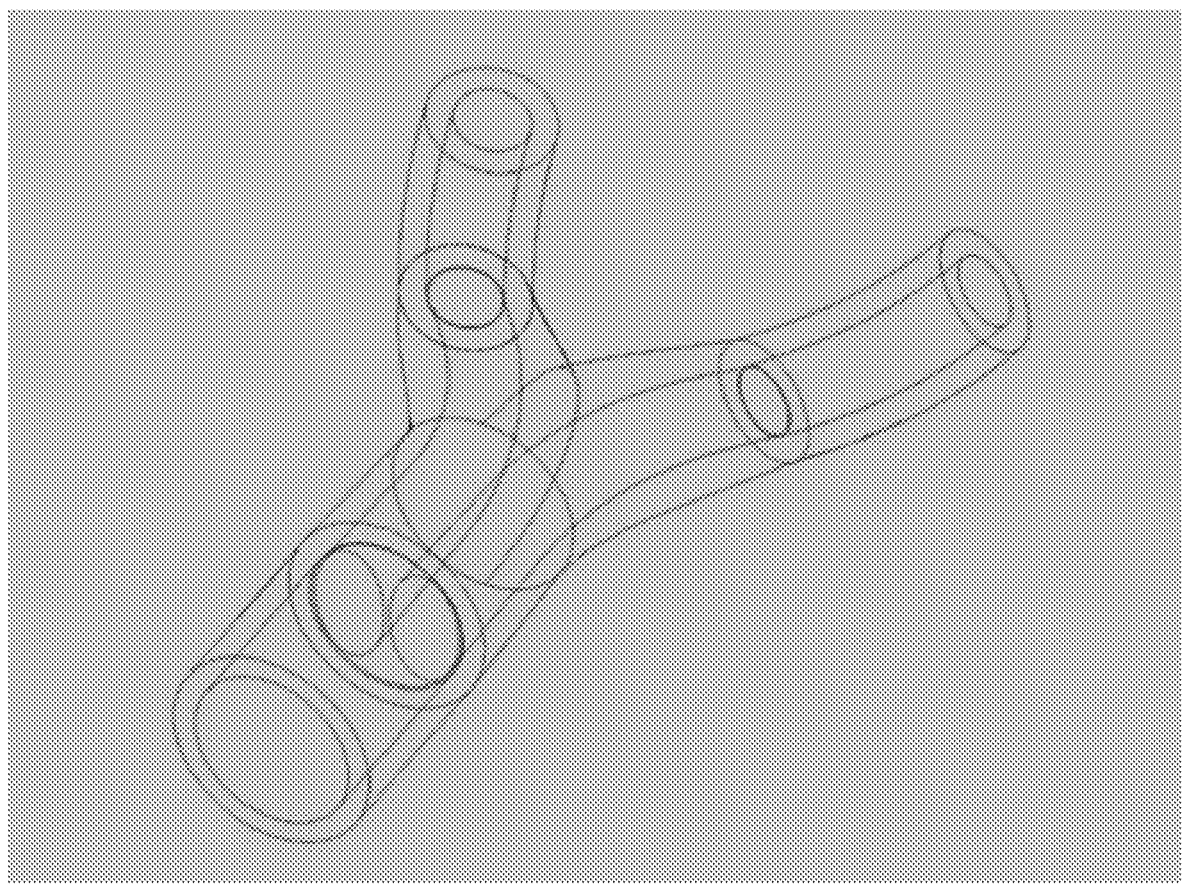
FIG. 6B is a wireframe view of the aortic bifurcation model with placed kissing stents.

The kissing stent procedural CAD model was created using similar techniques to that of the previous two bifurcations. Due to an expected presentation of 10-20 percent stenosis of the vessels upon the deployment of the stents, an aortic inner diameter of 20 mm and common iliac inner diameter of 9 mm were used for this model. The kissing stents were created with an ideal spline to resemble the most probable way in which stent would expand in the vessels. As the stents are fractions of a millimeter thick, they present small lips at their inlets and outlets. The inlet of blood flow from the distal aorta to the kissing stents is modeled as a flat face into two oval-opening stents, similar to the rendered image in FIG. 1. These kissing stents were held at a constant inner diameter throughout the stented portion of the model, with the exclusion of the inlet. The cross-section of this CAD model can be seen in FIG. 6A and a wireframe image of the entire model can be seen in FIG. 6B for clarity.

Figure 7A:
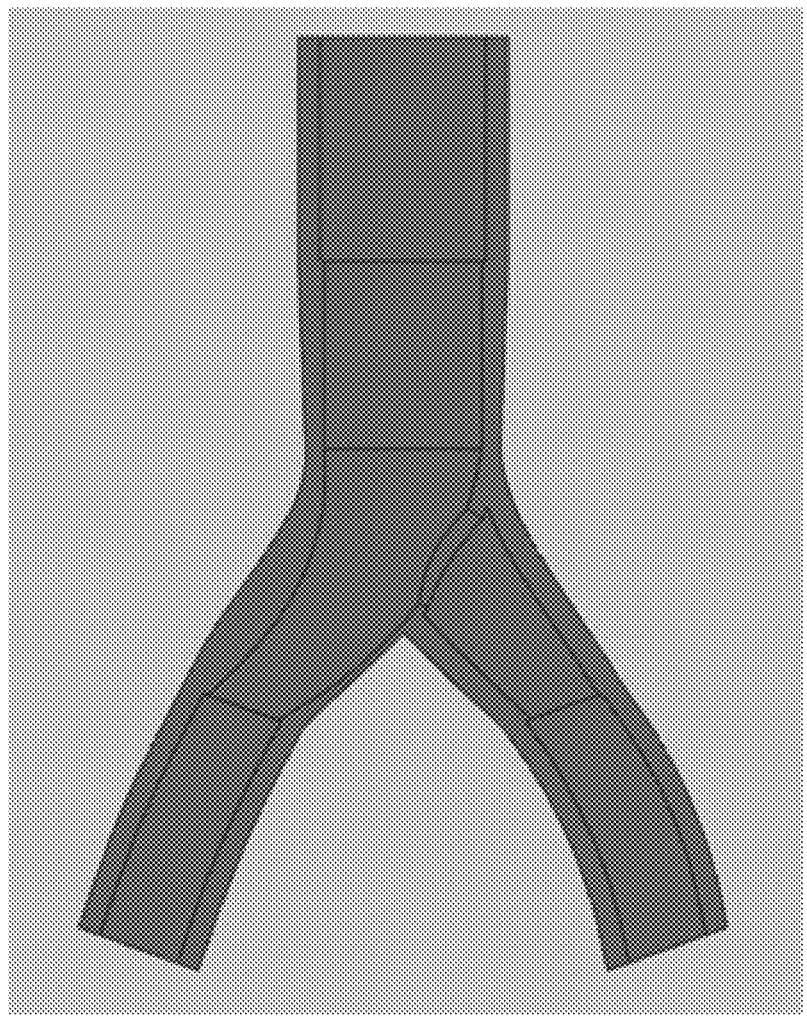
FIG. 7A is a cross-section of the aortic bifurcation model with the fenestrated stent design.
Figure 7B:
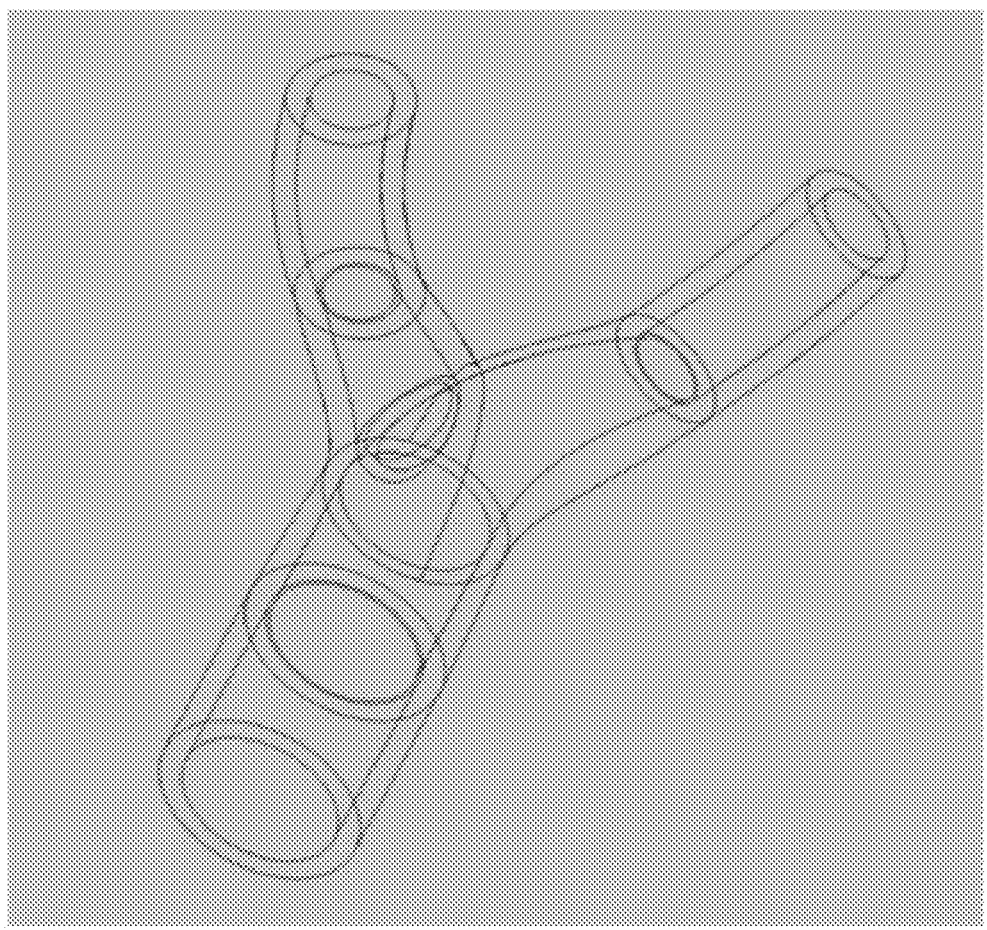
FIG. 7B is a wireframe view of the aortic bifurcation model with the fenestrated stent design.

To determine the optimal diameter of the fenestration in the ipsilateral main body stent, three CAD models of the fenestrated stents of varying diameter were utilized. These models differed from one another only in the diameter of the fenestration with diameters of 5, 10, and 15 mm. As in the kissing stent aortic bifurcation model, an aortic inner diameter of 20 mm and common iliac inner diameter of 9 mm were applied in all three models to represent the 10-20 percent stenosis of the vessels upon stent deployment. The complementary contralateral iliac stent was placed in the contralateral common iliac in a flared manner within the fenestration for the complete treatment of the aortic bifurcation. The complementary iliac stent was tapered from the flared fenestration to match the expected sizing of the contralateral common iliac artery. In contrast to the earlier models, the stents were not held at a constant inner diameter due to the device's tapered design. Each fenestrated stent was modeled upon a proper spline to most closely match the way the stent would deploy in the vessel. The cross-section of this CAD model can be seen in FIG. 7A and a wireframe image of the entire model can be seen in FIG. 7B for clarity.

Example 4: Boundary Conditions and Assumptions

For all models, the stent and arterial walls were assumed to be rigid. As the comparison of the ways by which the fenestrated stent and kissing stent procedures redirect blood flow was the focus of this study, the forces and shear placed on the vessel walls were neglected. Additionally, the inner walls of the stent and artery were modeled as smooth. Each stent was modeled such that the wire mesh lay on the outside of its plastic PTFE covering.

Boundary conditions were set for the inlet of the distal aorta, the outlets of the common iliac arteries, and the inner walls of each model. For the arterial wall and inner stent wall, the velocity was set to zero. For each of the common iliac artery outlets, a pressure of 100 mmHg was applied. For the inlet, a written inlet velocity function was used to simulate the phenomenon of blood pumping into the distal aorta. The scaling of this velocity plot was adjusted due to similar functions and results found in the literature. A representation of this function may be outlined by Fourier series:

$$v_{blood,inlet} = C_0 \left( \sum_{n=0}^{8} a_n \cos(nwt) + b_n \sin(nwt) \right) \quad \text{(Equation 1)}$$

Figure 8:
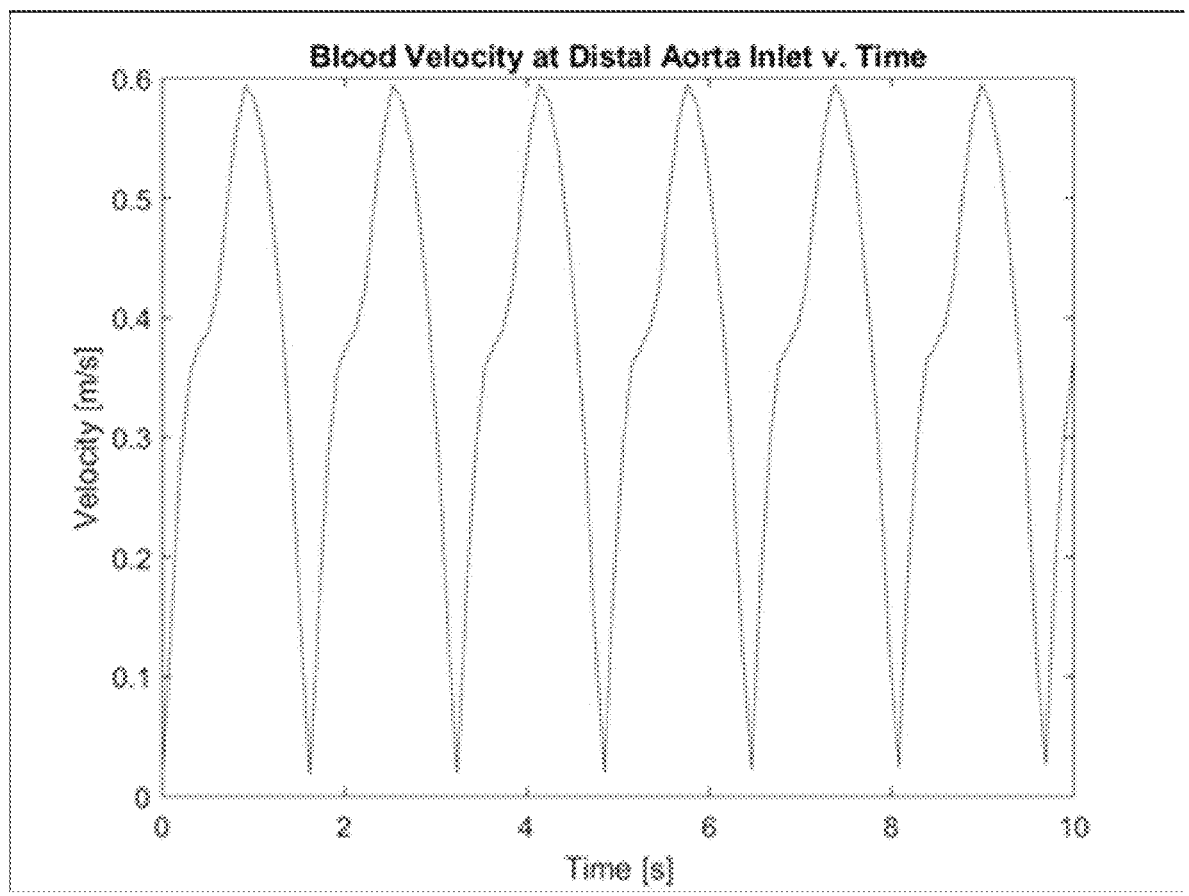
FIG. 8 is a plot of the blood velocity function entering the distal aorta inlet over time.

A plot of this blood velocity over time can be seen in FIG. 8.

Example 5: Discretization

The governing equations for each simulation utilized the continuity and Navier-Stokes equations. The applied continuity equation is as follows:

$$\frac{\partial \rho}{\partial t} + \nabla \cdot (\rho \vec{v}) = 0 \quad \text{(Equation 2)}$$

Such that $\rho$ is density, t is time, and v is velocity. However, as blood is assumed to be an incompressible fluid and thus density does not change as a function of time, the equation can be simplified to:

$$\nabla \cdot \vec{v} = 0 \quad \text{(Equation 3)}$$

The applied form of the Navier-Stokes equation is as follows:

$$\rho\left(\frac{d\vec{v}}{dt} + \vec{v} + \nabla \vec{v}\right) = -\nabla p + \mu \nabla^2 \vec{v} + \rho \vec{g} \quad \text{(Equation 4)}$$

Such that p is pressure, g is gravity, and μ is the dynamics viscosity coefficient. As blood is assumed to be a non-Newtonian fluid, the Carreau fluids model was applied to model the variable behavior of viscosity as a function of shear rate. This may be expressed mathematically as follows:

$$\mu_{\mathit{eff}}(\dot{\gamma}) = \mu_\infty + (\mu_0 - \mu_\infty)(1 + (\lambda\dot{\gamma})^2)^{\frac{n-1}{2}} \quad \text{(Equation 5)}$$

Where $\mu_{\mathit{eff}}$ is the effective viscosity, $\mu_\infty$ is the infinite-shear viscosity, $\mu_0$ is the zero-shear viscosity, n is the power-law index, λ is the time constant, and γ is the shear rate.

Example 6: Software and Experimental Parameters

All models were constructed utilizing SolidWorks (Dassault Systemes, Velizy-Villacoublay, France). This software utilizes a parametric feature-based approach to create 3D modeled parts. These six models of the aortic bifurcation were then imported into ANSYS Fluent for fluid dynamics calculations.

Fluent (ANSYS, Canonsburg, Pa., USA) is capable of modeling fluid flow, heat transfer, turbulence, and pressure gradients. This software was utilized in the analysis of blood flow through the models upon the application of stated boundary conditions, fluid and PTFE material properties. Data was collected in each model over a specified time step which was held constant. To minimize variability and internal error, each simulation was run multiple times and the results were compiled and standardized.

Figure 9:
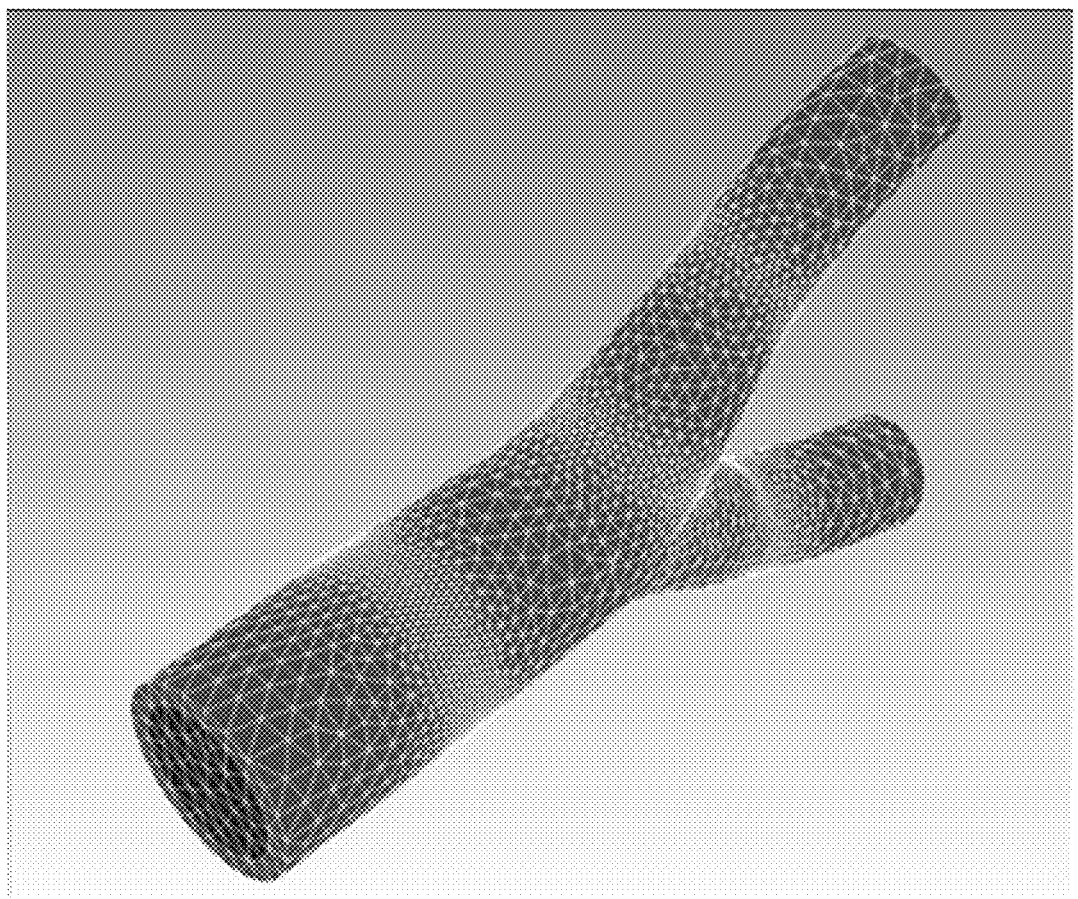
FIG. 9 is an isometric view of the mesh used for the fenestrated stent.

All experimental parameters are listed in Table 1. The CFD simulation in ANSYS Fluent was prepared using a pressure-based, absolute velocity solver in transient-state time. The experimental scheme was set to the default simple analysis structure and the applied spatial discretization included a least square cell-based gradient, second order pressure differential, and second order upwind momentum where the transient formulation was set to first order implicit. Additionally, default under-relaxation factors were applied, and the preprogrammed hybrid initialization method was selected. A sample image of the mesh used for the fenestrated stent can be seen in FIG. 9.

TABLE 1

Experiment parameters used throughout all fluidic simulations.

| | |
|---|---|
| Blood Density, $\rho_{blood}$ | 1060 kg/m$^3$ |
| Artery Density, $\rho_{artery}$ | 1160 kg/m$^3$ |
| Inner Stent, PTFE Density, $\rho_{PTFE}$ | 2200 kg/m$^3$ |
| Outlet Presure, $p_{out}$ | 100 mmHg |
| Time Constant, λ | 3.313 s |
| Power - Law Index, n | 0.3568 |
| Zero Shear Viscosity, $\mu_0$ | 0.056 kg/m · s |

TABLE 1-continued

Experiment parameters used throughout all fluidic simulations.

| | |
|---|---|
| Infinite Shear Viscosity, $\mu_\infty$ | 0.0035 kg/m · s |
| Mesh Size | 200,000-500,000 elements |
| Time Step | 0.1 s |
| Time Span | 20 s |

Example 7: Parametric Studies

Data was compiled for each of the six aortic bifurcation models, including the average velocity at inlets and outlets, velocity and vorticity, and the location of points of stagnation via vorticity mapping. As the design of the fenestrated stent seeks to minimize vorticity, stagnation, evenly distribute outlet mass flow rates, normalize outlet velocities, minimize pressure concentrations, and developed ideal streamline conditions, an optimization experiment was conducted by comparing the three fenestration designs for the AIFEN stent model of varying diameters.

Example 8: Flow Analysis

CFD simulations were performed in the ANSYS Fluent environment to assess the performance of the kissing and AIFEN stenting procedures, with healthy and unhealthy bifurcations acting as a control group. The vorticity of the fluid flowing through each model was mapped to highlight regions of flow agitation and stagnation which may lead to thrombosis and occlusion. These vorticity maps are compared in FIG. 19A, FIG. 19B, FIG. 19C, FIG. 19D, FIG. 19E, and FIG. 19F.

Example 9: Tabulated Data

Table 2 displays the mass flow rate data from the all simulations. Outlet-1 remained the common iliac artery exit which received flow through the fenestration in the ipsilateral main body stent for the fenestrated stent models.

TABLE 2

Average Outlet Mass Flow Rate

| | Mass Flow Rate (kg/s) | | Variation from Healthy Bifurcation (kg/s) | |
|---|---|---|---|---|
| Model | Outlet-1 | Outlet-2 | Outlet-1 | Outlet-2 |
| Healthy Bifurcation | 0.0798 | 0.0792 | — | — |
| Unhealthy Bifurcation | 0.0802 | 0.0788 | 0.0004 | 0.0004 |
| Ideal Kissing Stents | 0.0795 | 0.0794 | 0.0003 | 0.0002 |
| AIFEN Stent, 5 mm | 0.0959 | 0.0631 | 0.0161 | 0.0161 |
| AIFEN Stent, 10 mm | 0.0822 | 0.0768 | 0.0024 | 0.0024 |
| AIFEN Stent, 15 mm | 0.0804 | 0.0786 | 0.0006 | 0.0006 |
| Inlet Mass Flow Rate Constant 0.159 kg/s | | | | |

Table 3 displays the velocity data from all simulations. Outlet-1 was again maintained as the contralateral iliac artery for the fenestrated stent models.

TABLE 3

Average Outlet Velocity

| Model | Mass Flow Rate (kg/s) | | Variation from Healthy Bifurcation (kg/s) | |
|---|---|---|---|---|
| | Outlet-1 | Outlet-2 | Outlet-1 | Outlet-2 |
| Healthy Bifurcation | 0.457 | 0.459 | — | — |
| Unhealthy Bifurcation | 0.937 | 0.932 | 0.48 | 0.473 |
| Ideal Kissing Stents | 0.5496 | 0.5556 | 0.0926 | 0.0966 |
| AIFEN Stent, 5 mm | 0.5602 | 0.3593 | 0.1032 | 0.0997 |
| AIFEN Stent, 10 mm | 0.4715 | 0.4454 | 0.0145 | 0.0136 |
| AIFEN Stent, 15 mm | 0.462 | 0.456 | 0.005 | 0.003 |

Inlet Velocity Constant 0.2264 m/s

Example 10: Mass Flow Rate

The outlet mass flow rate of each model was evaluated to compare their relative ability to evenly distribute blood flow between the iliac artery outlets and to compare the observed outlet mass flow rates to the healthy bifurcation control. For the symmetrical healthy aortic bifurcation model, the average mass flow rates from the outlets were observed to be between 0.0798 and 0.0792 kg/s for the collateral and contralateral outlets, respectively. The outlet mass flow rates in the unhealthy aortic bifurcation model were 0.082 and 0.0788 kg/s for the collateral and contralateral outlets, respectively.

Due most likely to design asymmetry and rigid analysis, the 5 mm OD fenestrated AIFEN model demonstrated the most pronounced variation in mass flow rates compared to the healthy bifurcation control, varying by 0.0161 kg/s from each outlet. This amount of error would be deemed unacceptable to treat the aortic bifurcation, thus providing initial indications that the 5 mm fenestration is too small.

Increasing the OD of the AIFEN fenestration demonstrated progressively improved performance, with the mass flow rates from both outlets of the 15 mm OD fenestration varying by 0.0006 kg/s from the healthy bifurcation control. While the ideal kissing stent model demonstrated mass flow rate variation of 0.0003 and 0.0004 kg/s via outlet 1 and 2 respectively, it is noted that this is mostly likely due to this model consisting of two pipes of equal length deployed in practically unachievable symmetry with no constriction along their length. As such, this model presented a "better than perfect" scenario, with outlet mass flow rates more closely achieving the ideal value of 0.0795 kg/s, ½ the inlet mass flow rate of 0.159 kg/s, than the healthy bifurcation control which contained more realistic flow conditions.

Overall, the 15 mm model displayed superior performance among the fenestrated trial models of varied diameter, and it is hypothesized that further improvements may be achieved by tailoring the diameters of the two arms of the fenestrated stent as well as the angle of approach for the fenestration itself. It is noted that the AIFEN models of increasing fenestration OD more closely resemble the shape and flow conditions of the healthy bifurcation control, as may be observed in FIG. 19A, FIG. 19D, FIG. 19E and FIG. 19F. As it is the goal of this procedure to restore patency to the aortoiliac bifurcation, restoring the occluded bifurcation to a shape most closely resembling its pre-diseased state may lead to optimal outcomes.

Example 11: Average Outlet Velocity

In analyzing the simulations, the maximum Reynold's number for fluid flow was recorded in each case. Reynold's numbers of 350, 453, and 488 were observed for the healthy bifurcation, unhealthy bifurcation, and ideal kissing stents respectively. Reynold's numbers of 594, 488, and 891 were observed for the proposed AIFEN stents with 5, 10, and 15 mm OD fenestrations respectively. As all values are lower than 2,000, laminar fluid flow may be assumed.

It was observed that these initial boundary condition velocities were accelerated by the narrowing of the aortic bifurcation, as fluid velocity is expected to increase when flowing into a region of decreased diameter. For the symmetrical healthy aortic bifurcation model, the average flow velocities from the outlets were observed to be between 0.457 and 0.459 meters per second for the collateral and contralateral outlets, respectively. The outlet velocities in the unhealthy aortic bifurcation model were nearly double this, ranging between 0.937 and 0.932 meters per second for the collateral and contralateral outlets, respectively. These results were used to establish a fundamental range of physiological to pathophysiological velocity fields with which to compare the arterial stenting designs.

The kissing arterial stenting model displayed a decreased outlet velocity in comparison to the unhealthy aortic bifurcation, with observed average velocities of 0.5496 and 0.5556 meters per second for the collateral and contralateral outlets, respectively, but did not decrease these to the levels of the healthy aortic bifurcation model from which they each varied by nearly 0.1 meters per second. While the 5 mm OD fenestration demonstrated the comparatively worst values of 0.5602 and 0.3593 meters per second for the collateral and contralateral outlets, respectively, the AIFEN models improved dramatically with increasing fenestration OD. The 10 mm OD fenestration AIFEN model demonstrated outlet velocities of 0.4715 and 0.4454 meters per second from the collateral and contralateral outlets, respectively, while the 15 mm OD fenestration AIFEN model exhibited the most comparably optimal values of 0.462 and 0.456 meters per second for the collateral and contralateral outlets, respectively, differing from the healthy bifurcation control by 0.005 and 0.003 meters per second.

The attenuated peak velocities in the 15 mm fenestrated stent model were notedly promising and suggest that the design warrants further investigation. While it is noted that the expected distortion of the bifurcation during heart palpitation was not modeled in this study, it may be inferred from these results that the design of the fenestrated stent provides a smooth transition of blood flow in the bifurcation from the distal aorta to the common iliac arteries. Provided that the pressure is maintained as constant throughout the aortic bifurcation, this reduction in peak average velocity represents a favorable outcome of the 15 mm model over the kissing arterial stenting procedure.

Example 12: Vorticity

Vorticity contour plots were generated to determine if any turbulence or stagnation was occurring, particularly in the stented aortic bifurcation models as may be seen in FIG. 19A, FIG. 19B, FIG. 19C, FIG. 19D, FIG. 19E, and FIG. 19F. For the healthy and unhealthy aortic bifurcation models, vorticity conditions were considered trivial due to their smooth surfaces and symmetric modeling, wherein no focal points of vorticity could be found.

Examining the vorticity of the kissing stent aortic bifurcation model, peak values, in units of radians per second, were observed with focal points at the inlets and outlets of the stents. As a comparably great deal of vorticity is focused at these points, a subsequent reversal in the direction of flow and the thrombosis of blood would be expected there. This further demonstrates potential hazards presented by the kissing stent procedure, even in this practically unachievably optimal state.

The AIFEN models demonstrated decreasing amounts of vorticity for increasing fenestration OD. The 5 mm OD fenestration AIFEN demonstrated the most vorticity among the AIFEN models, with a large amount of vorticity observed around the internal edge of the contralateral complementary iliac stent, likely due to the difference in diameter causing flow to accelerate. The 10 mm fenestration model demonstrated points of vorticity toward the end of the contralateral complementary iliac stent, though further "downstream" and to a lesser effect than that observed in the 5 mm OD fenestration AIFEN, due most likely to the curve of the contralateral complementary iliac stent causing the flow to shift direction suddenly.

Lastly, the 15 mm fenestrated model demonstrated results comparably superior to the 5 and 10 mm fenestration models, in addition to the kissing stent procedural model. This is a result of significant portions of vorticity being reduced through the complementary common iliac vessel and at the inlet of the ipsilateral main body stent, suggesting that the 15 mm fenestration design presents a substantial improvement over the current standard of care. As was previously noted, the AIFEN models more closely resemble the shape of the healthy aortoiliac bifurcation with increasing fenestration OD compared to the kissing stent model and may consequently offer superior means by which to restore aortoiliac patency.

Summary of Examples 1-12

Computer-aided design models of healthy and unhealthy aortic bifurcations were used to establish a range of acceptable values and outcomes, which were then compared to three fenestrated models of varying diameter. This was done using velocity contour plots and velocity vector maps generated via a non-Newtonian blood pulsating flow simulation. Results suggested significant improvements over the commonly applied kissing stents angioplasty method with a novel fenestrated stent angioplasty treatment option. The most notable evidence in favor of the fenestrated stent approach lay in the noted reduction in substantial issues present in the kissing stents model such as flow stagnation and consequent thrombus formation. In addition, outlet flow velocities and mass flow rates demonstrated superior outcomes, in favor of the 15 mm fenestration model. It is argued that this new fenestrated stenting technique of the aortic bifurcation demonstrates potential for superior performance in addressing a serious and life-threatening disease.

Further optimization of the proposed fenestrated stent may be conducted to maximize the effects of its application. The fenestration should be the main focal point of next-phase design aims, as it must allow for a more evenly distributed mass blood flow from the distal aorta through both iliac arteries. Additionally, a smoother transition of blood into the fenestration may decrease the likelihood of the formation of high velocity focal points around the internal edge of the contralateral complementary iliac stent. Further analysis may also incorporate deformable bodies to allow for a more realistic response from the aortic bifurcation. With a more optimized method of blood flow transition into the contralateral iliac artery, this stent may be prepared for implementation into the surgical industry.

Example 12: Additional CFD Simulations

CFD simulations were performed in the ANSYS Fluent environment to assess the performance of the kissing and fenestrated arterial stenting procedures. Flow fields at a healthy and an unhealthy bifurcation were first estimated as a comparison case.

Figure 10A:
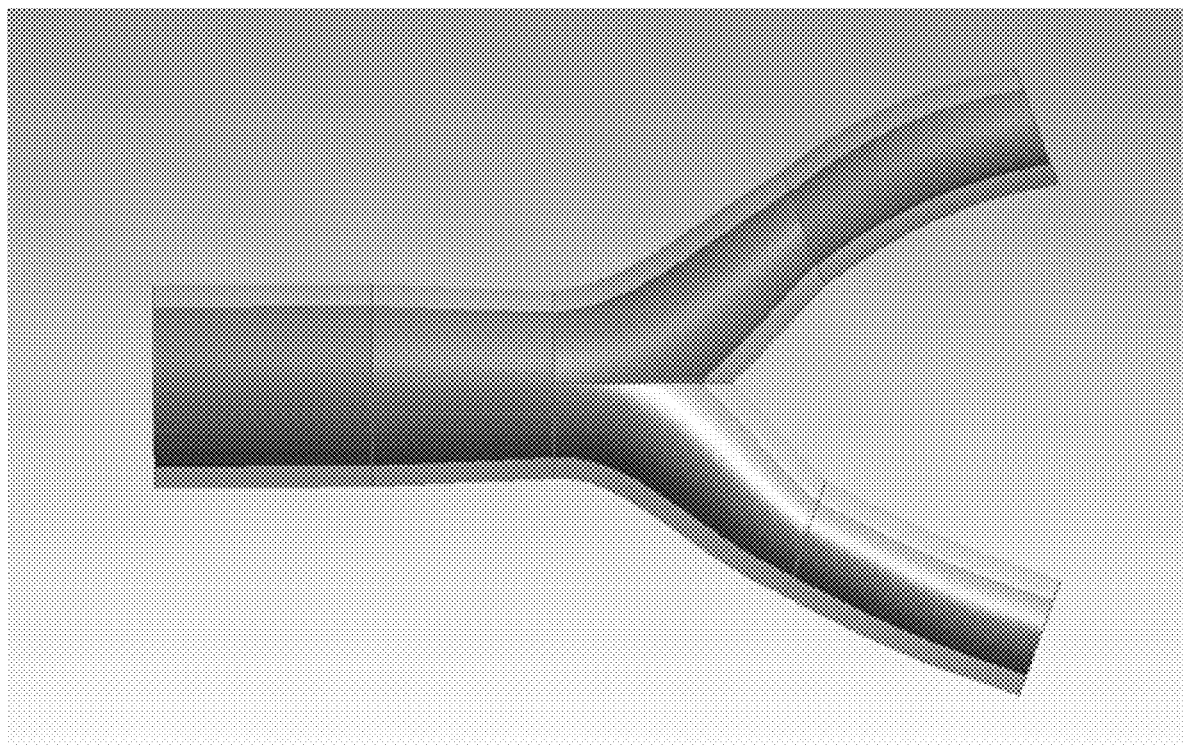
FIG. 10A is a model of the fluid fill of the healthy aortic bifurcation.

FIG. 10A displays the inner fill used to simulate the healthy aortic bifurcation. The healthy aortic bifurcation model was used in order to create a fundamental understanding of the best-case scenario of results that the flow would produce. The velocity contour map (FIG. 10B) of the healthy aortic bifurcation showed the expected symmetric velocity field. The peak velocity magnitudes over the course of a cycle occurred near the exits and reached a maximum of 1.33 meters per second. The vorticity field in the healthy aortic bifurcation was similarly symmetrical (FIG. 10C). Over the course of cardiac cycle, the vorticity showed a peak value near the exits of 2930 radians per second. Finally, the streamlines in the healthy aortic bifurcation, which represent the magnitude and directionality of the dimensional velocity field, largely followed the inner contours of the aorta, with some mixing at the bifurcation, as seen in FIG. 10D.

Figure 11A:
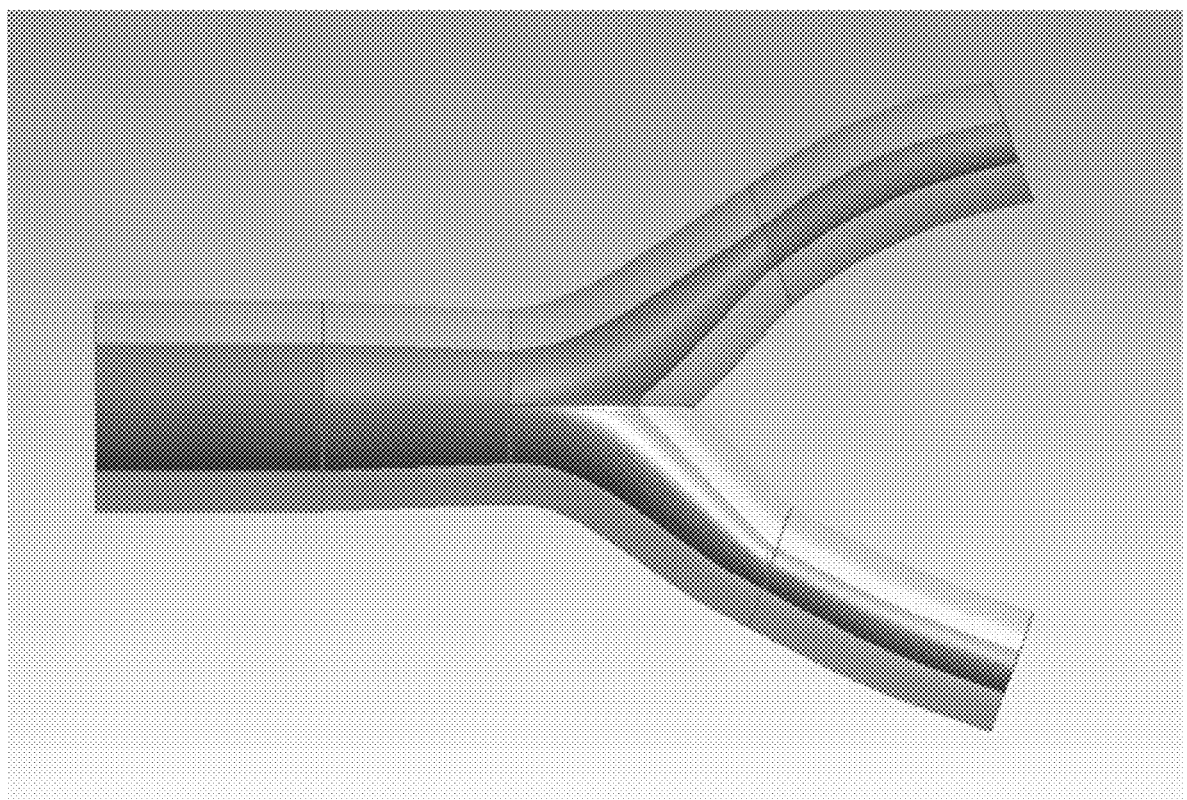
FIG. 11A is a model of the fluid fill of the unhealthy aortic bifurcation.

The flow fields in the idealized unhealthy aortic bifurcation (FIG. 11A) were studied as a worst-case comparison situation. Velocity (FIG. 11B) and vorticity (FIG. 11C) fields were qualitatively similar to those of the healthy bifurcation, as were the streamlines (FIG. 11D). However, the magnitudes were different. The peak velocity through the constricted aorta increased to 2.78 meters per second, and the peak vorticity increased to 12200 radians per second.

Figure 12A:
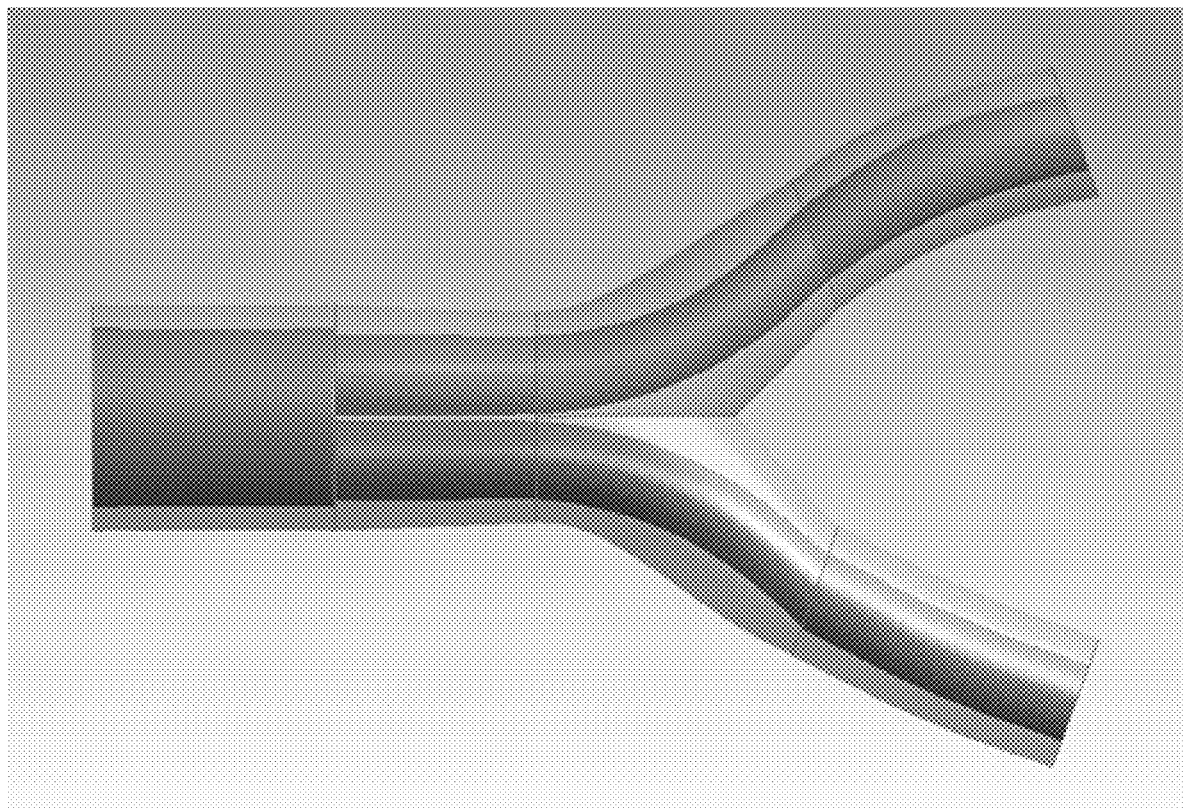
FIG. 12A is a model of the fluid fill of the kissing stent aortic bifurcation model.

The kissing arterial stenting angioplasty procedure (FIG. 12A) altered the flow fields from the two baseline cases. Velocity contours (FIG. 12B) showed a sharp acceleration at the stent bifurcation and a peak velocity of 1.86 meters per second was recorded. Superimposing the image of the stent (FIG. 12C) revealed a change of flow direction occurring the near the inlet of the two kissing stents in the distal aorta. Vorticity fields (FIG. 12D) showed a maximum vorticity of 10800 radians per second. Streamlines largely followed the stent contours (FIG. 12E).

Figure 13A:
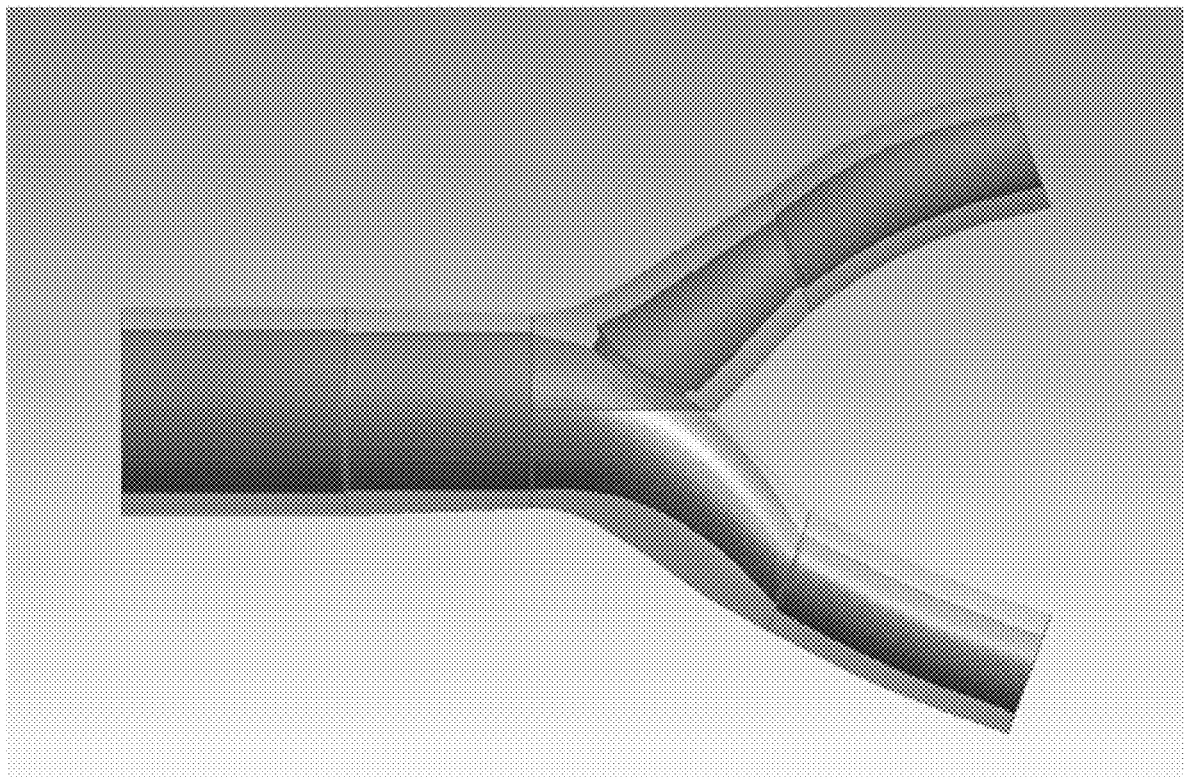
FIG. 13A is a model of the fluid fill of the fenestrated stent aortic bifurcation model.
Figure 13B:
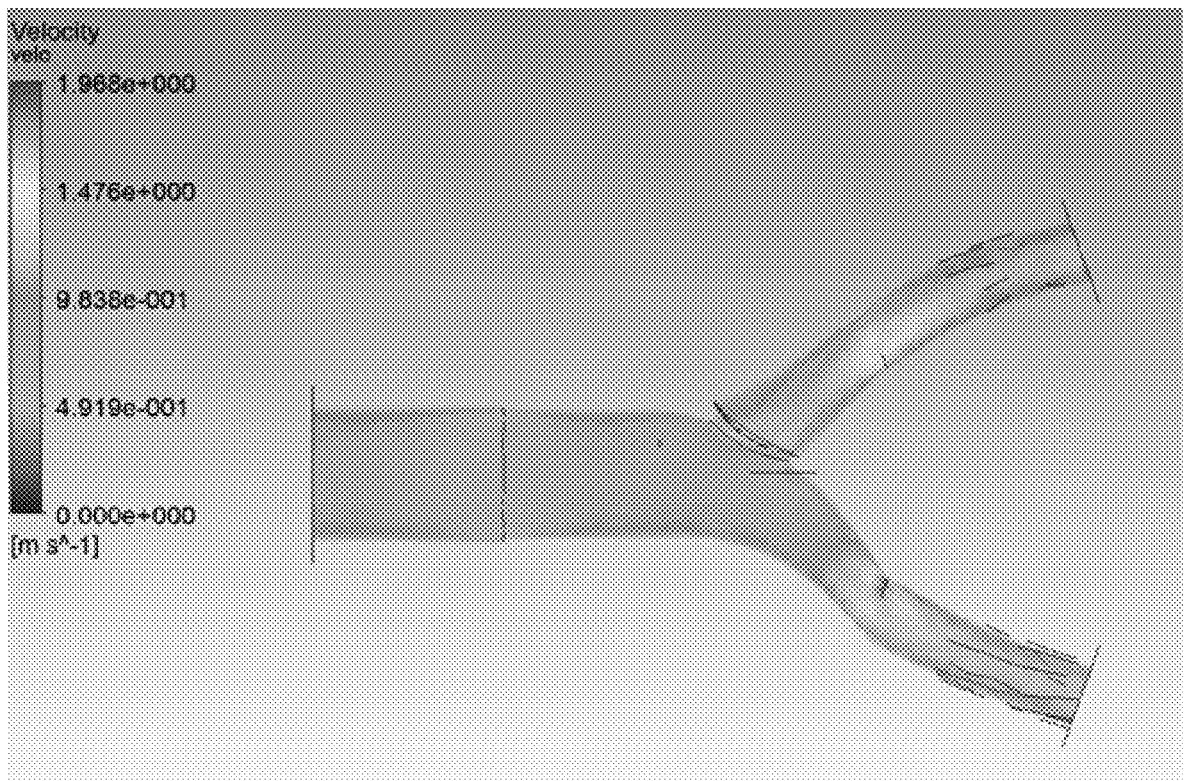
FIG. 13B is a model of the velocity contour of the fenestrated stent aortic bifurcation model.

The fenestrated arterial stenting procedure (FIG. 13A) was studied as a potential intervention for aortoiliac occlusive disease. The velocity contours showed a maximum velocity of 1.97 meters per second, but did not show flow direction change (FIG. 13B, 13C) when the image of the stent was superimposed over the flow field. Peak vorticity (FIG. 13D) reached 10800 radians per second. Streamlines (FIG. 13E) showed minor perturbations around kinks in the stents.

Example 13: Velocity Contour Plots, Vectors, and Streamlines

Due to meshing and modeling conditions, CFD simulations occasionally predict anomalously larger velocities, pressures, and other field variables at sharp corners and quick changes in diameter. To avoid artifacts, a careful analysis was done to observe the velocity and vorticity contour plots. This enabled determination of whether stagnation or undesirable flow occurred along the length of the bifurcation model.

Figure 10B:
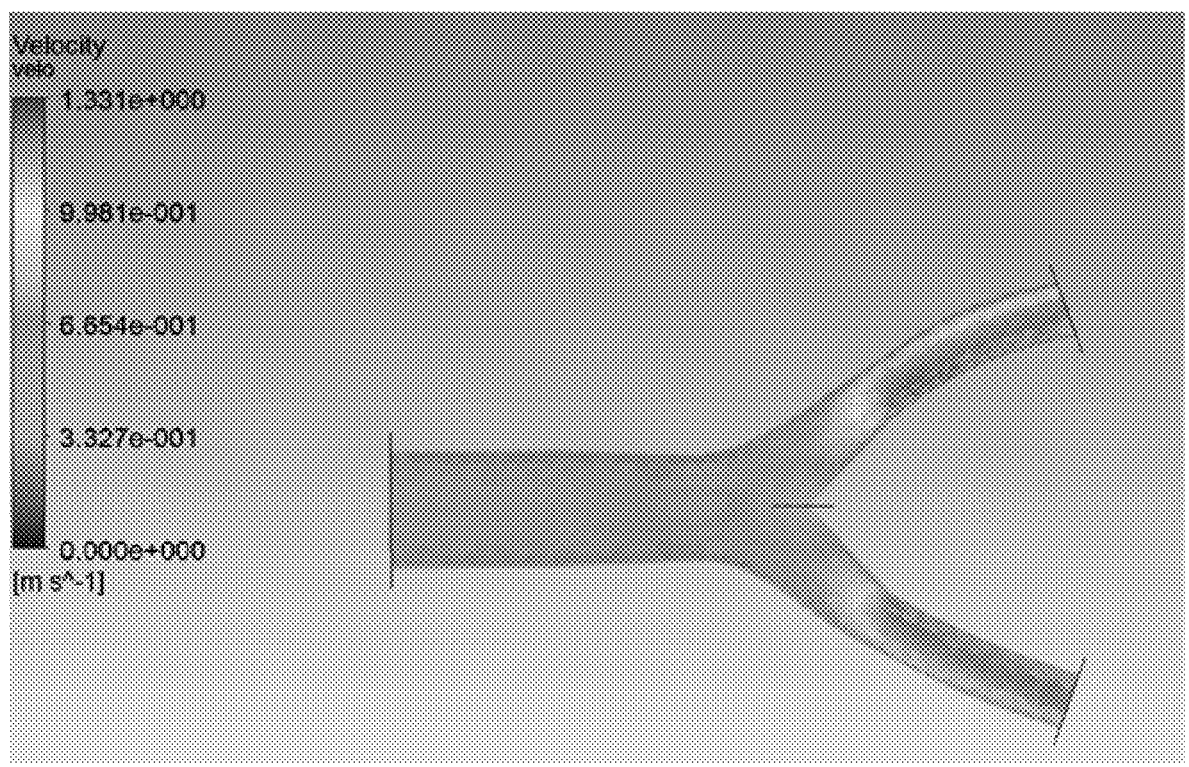
FIG. 10B is a model of the velocity contours within a healthy aortic bifurcation.
Figure 10C:
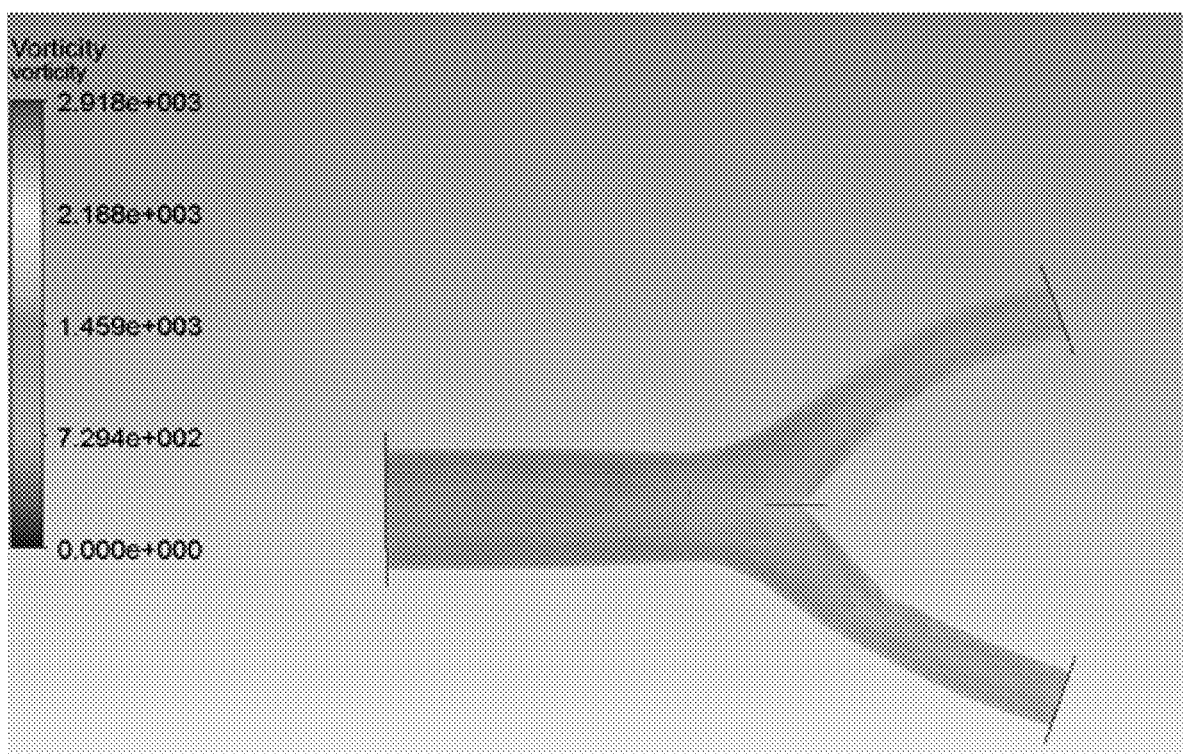
FIG. 10C is a model of the vorticity of the healthy aortic bifurcation.
Figure 10D:
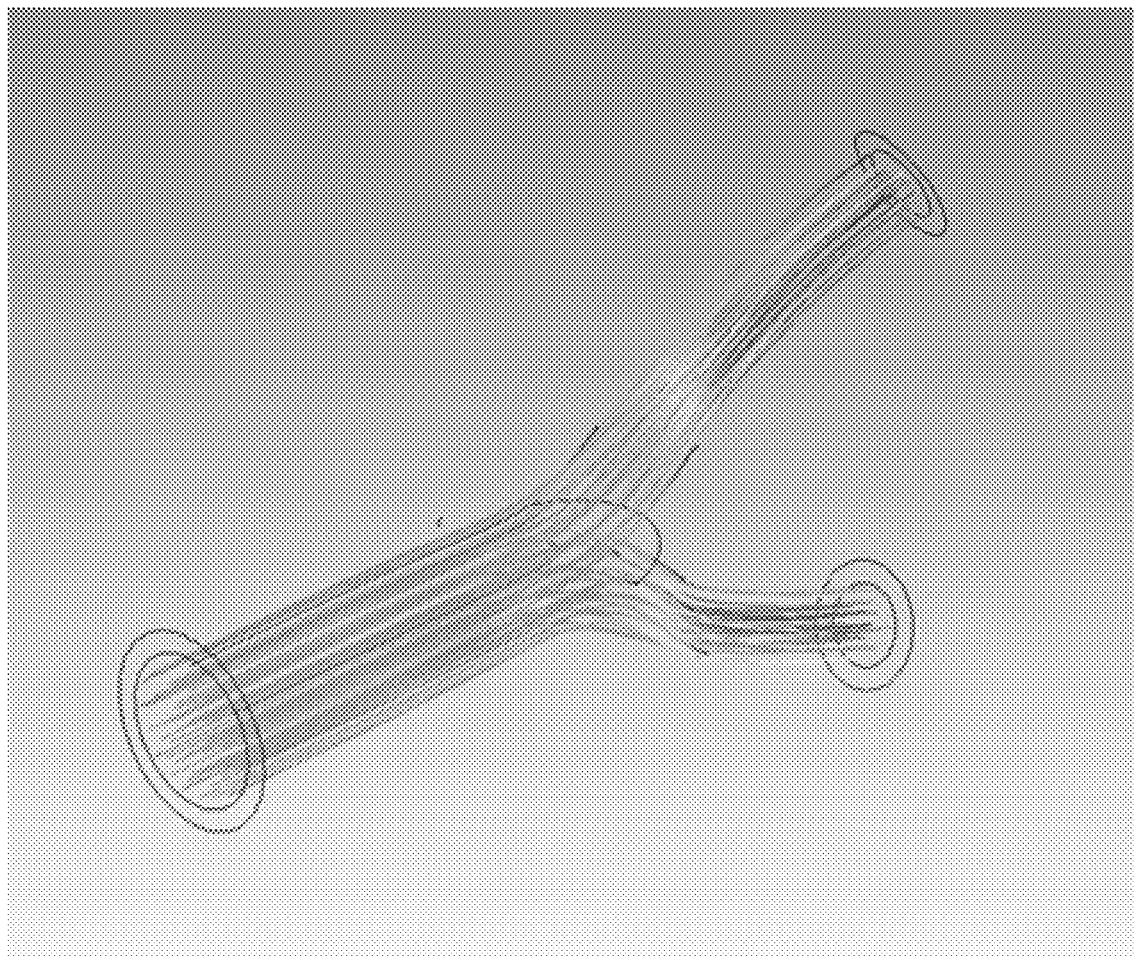
FIG. 10D is a model of the velocity streamlines of the healthy aortic bifurcation.

The healthy aortic bifurcation, in FIG. 10B, showed a gradual velocity towards the center of the vessel near 0.6 meters per second in the distal aorta. This matches the blood flow inlet function that has a peak velocity around approximately 0.6 meters per second. The model shows a steady increase in velocity to approximately 1 meter per second in the common iliac arteries, closely matching the literature. Additionally, zero velocity was seen at the walls due to the set boundary condition. No reverse flows (negative velocities) were observed, meaning that no flow separation or turbulence occurred. The streamlines of this model, in FIG. 10D, represented this in a similar fashion.

Figure 11B:
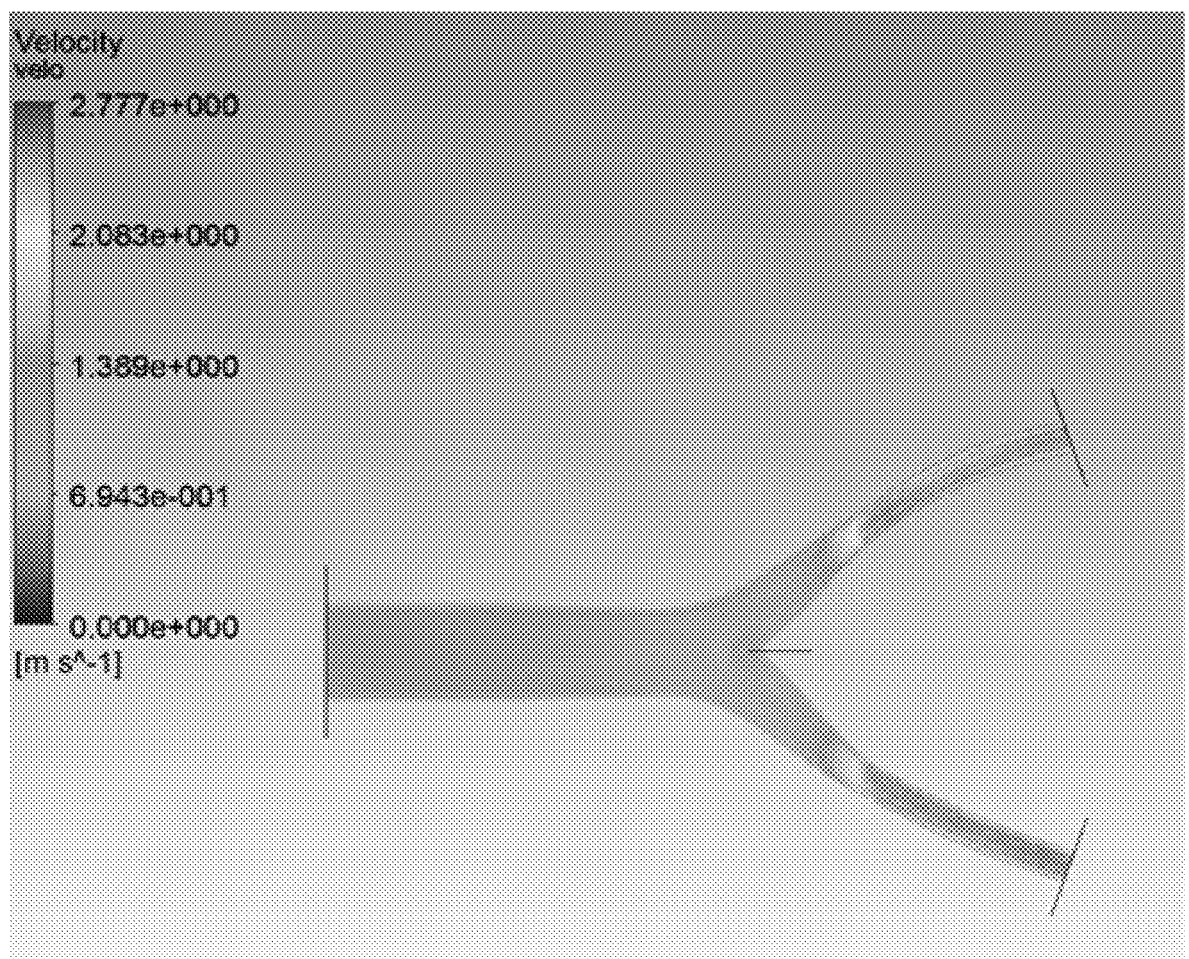
FIG. 11B is a model of the velocity contour of the unhealthy aortic bifurcation.
Figure 11C:
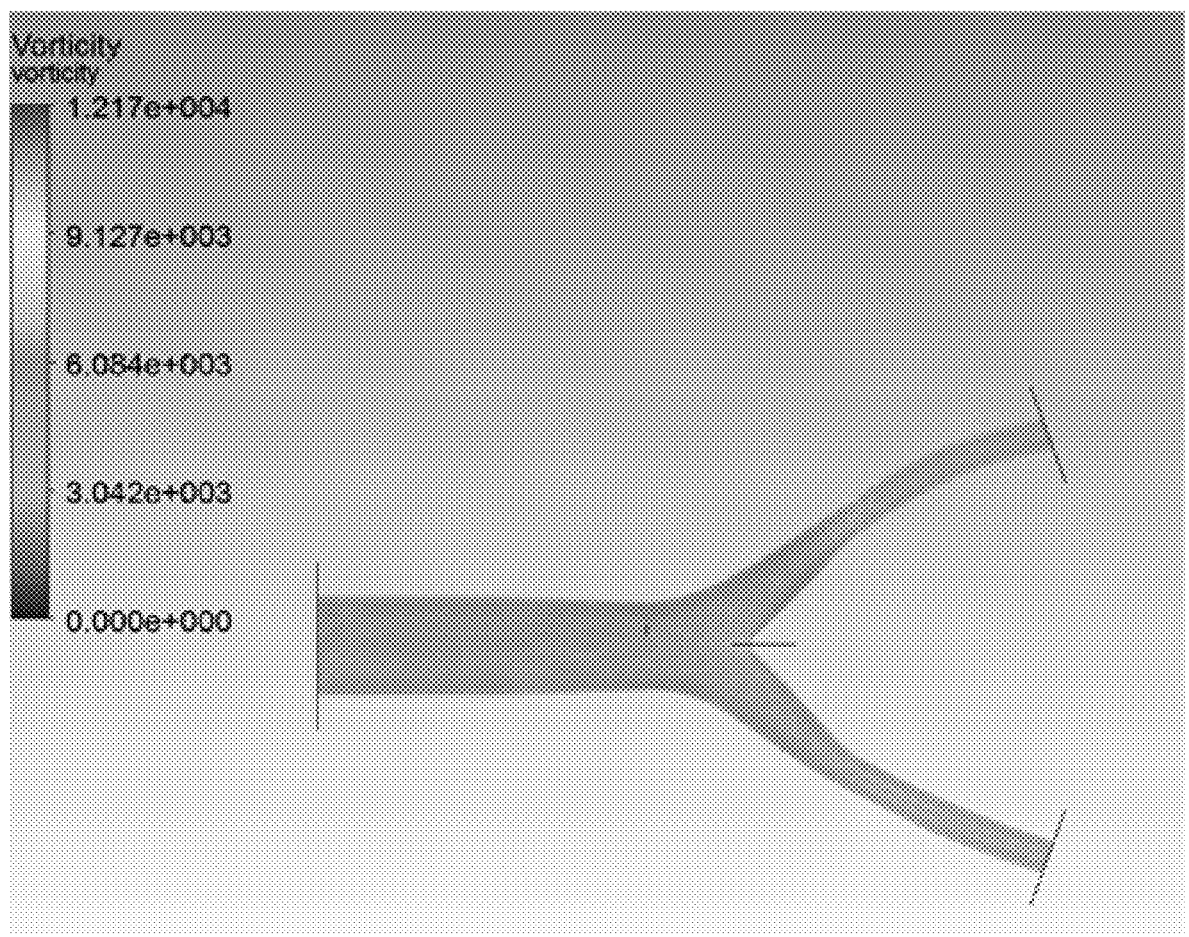
FIG. 11C is a model of the vorticity of the unhealthy aortic bifurcation.
Figure 11D:
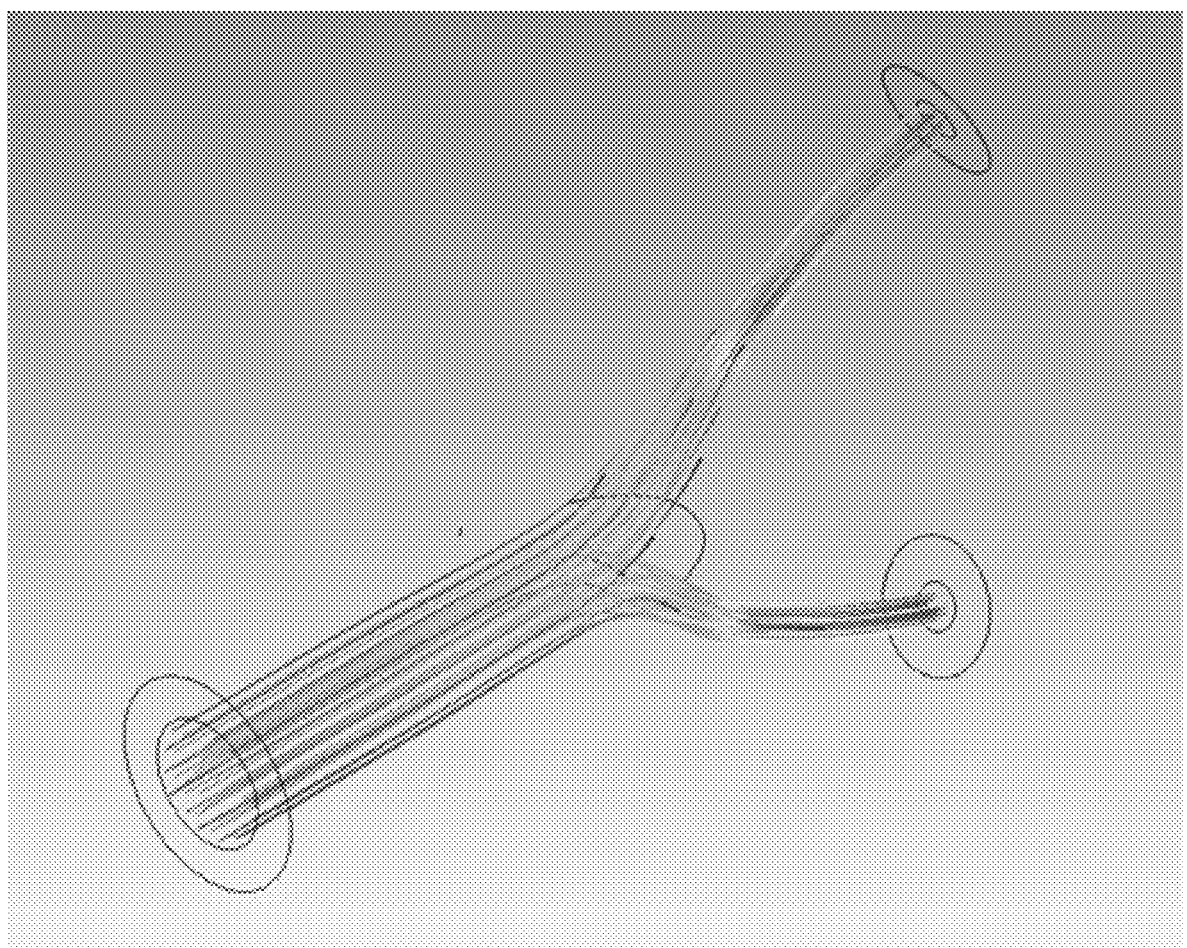
FIG. 11D is a model of the velocity streamlines of the unhealthy aortic bifurcation.

The unhealthy aortic bifurcation model, in FIG. 11B, performed nearly identical to the healthy aortic bifurcation model. However, using the velocity color scale to evaluate the magnitude of the velocities, there was a small increase in velocity in the distal aorta in comparison to the healthy bifurcation model. The common iliac arteries show a velocity flow that is over double that of the healthy bifurcation. These results are expected as the unhealthy bifurcation has inner diameters that are nearly half of the healthy bifurcation. The rigid assumption of these vessels could of possibly impacted velocity as, normally, some of this energy would be transferred to the arteries themselves. The streamlines representation of the unhealthy aortic bifurcation model, FIG. 11D, matched this representation as well.

Figure 12B:
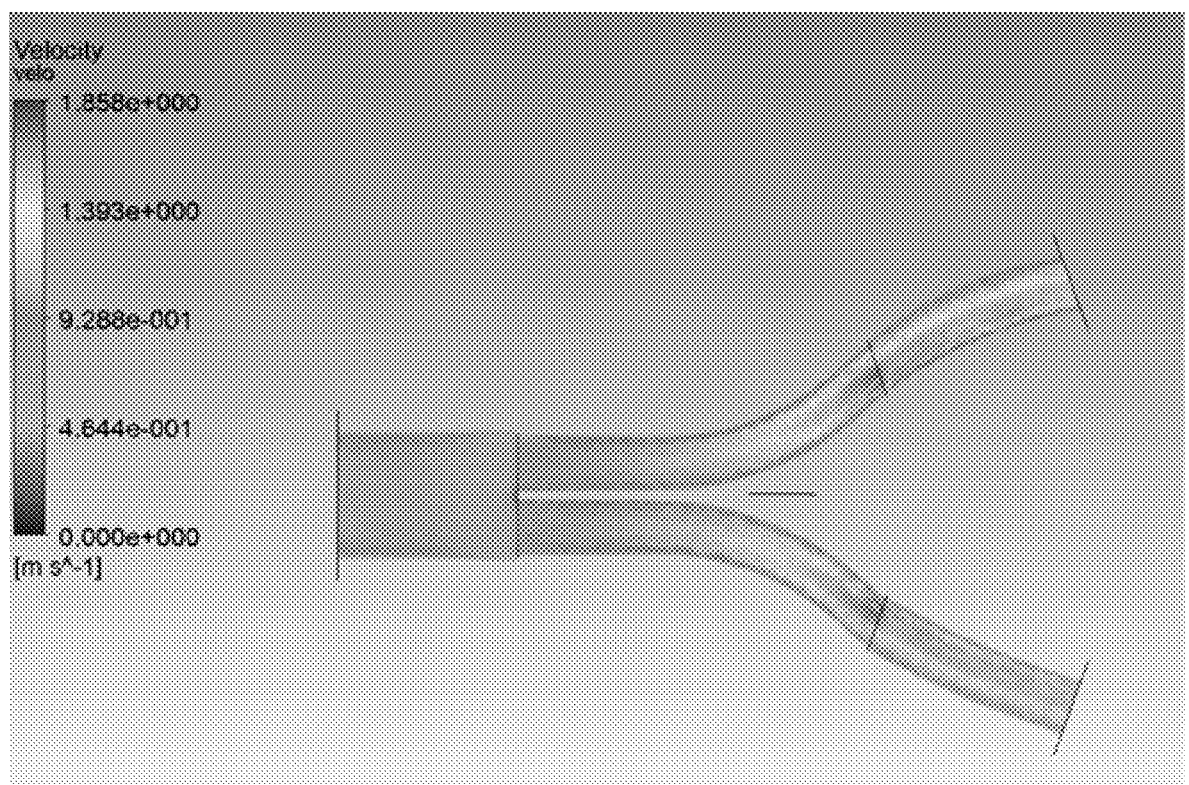
FIG. 12B is a model of the velocity contour of the kissing stent aortic bifurcation model.
Figure 12C:
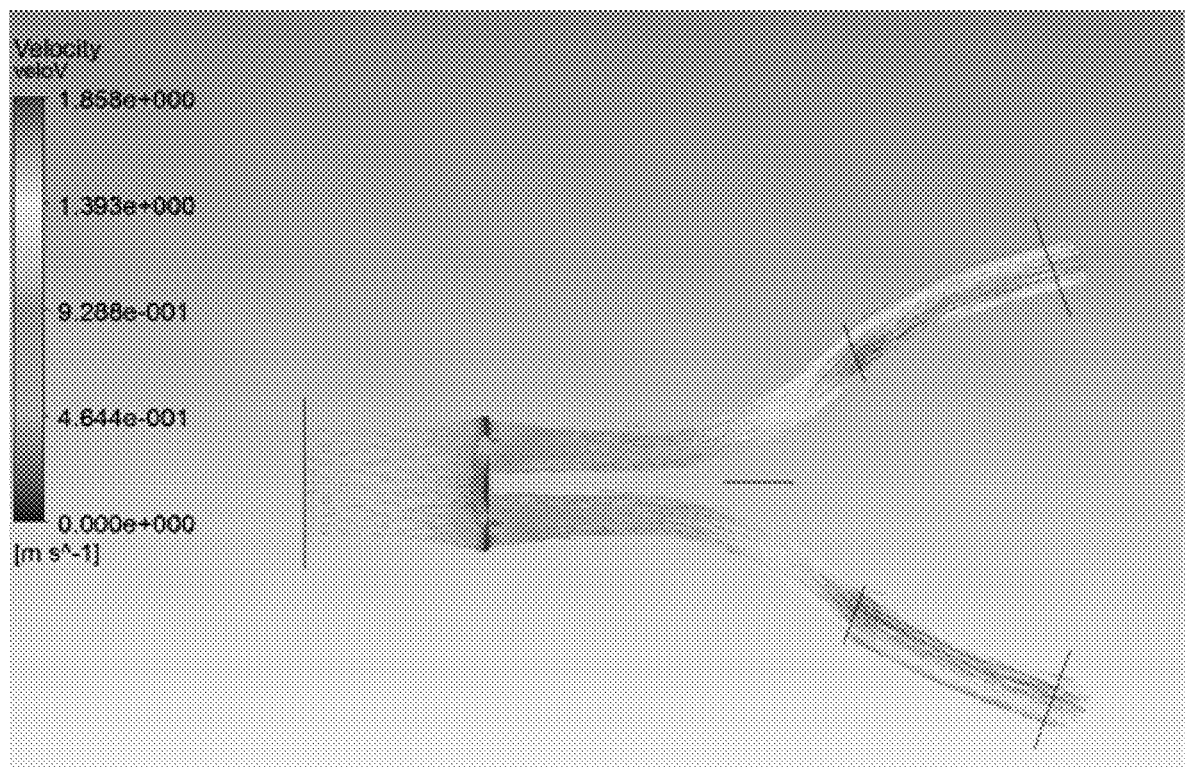
FIG. 12C is a model of the velocity vector map of the kissing stent aortic bifurcation model.
Figure 12D:
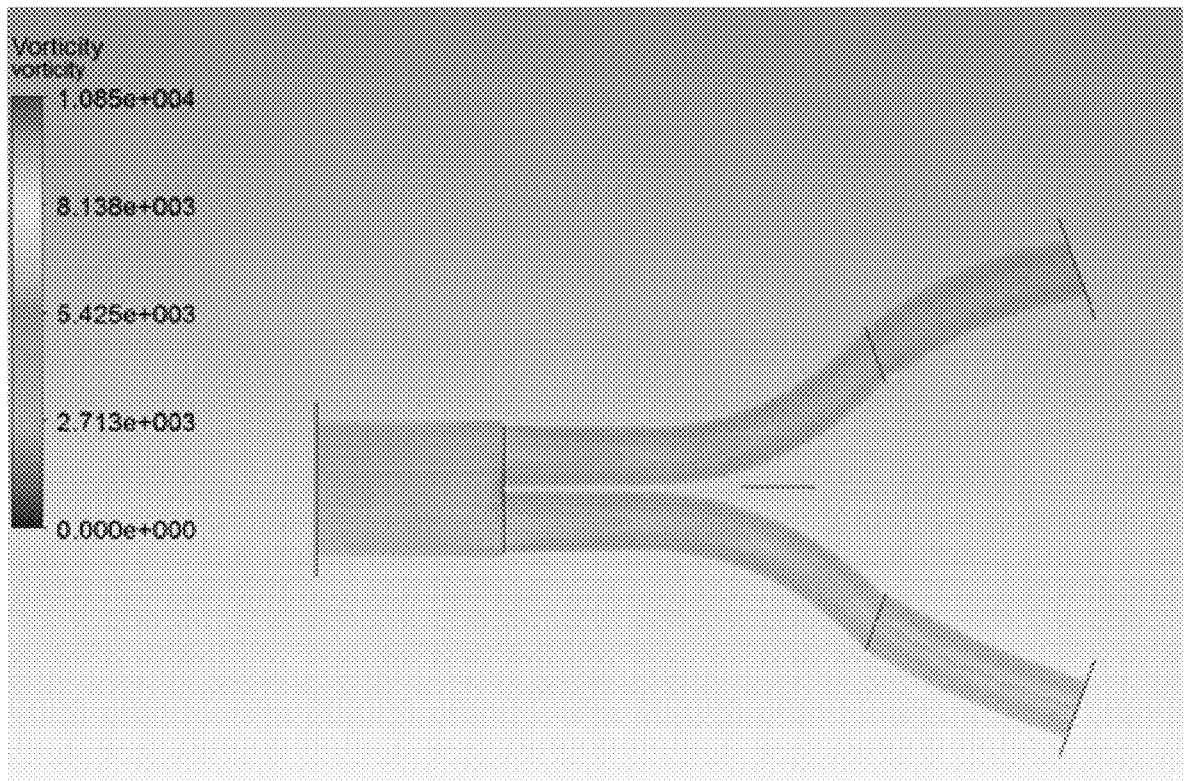
FIG. 12D is a model of the vorticity of the kissing stent aortic bifurcation model.
Figure 12E:
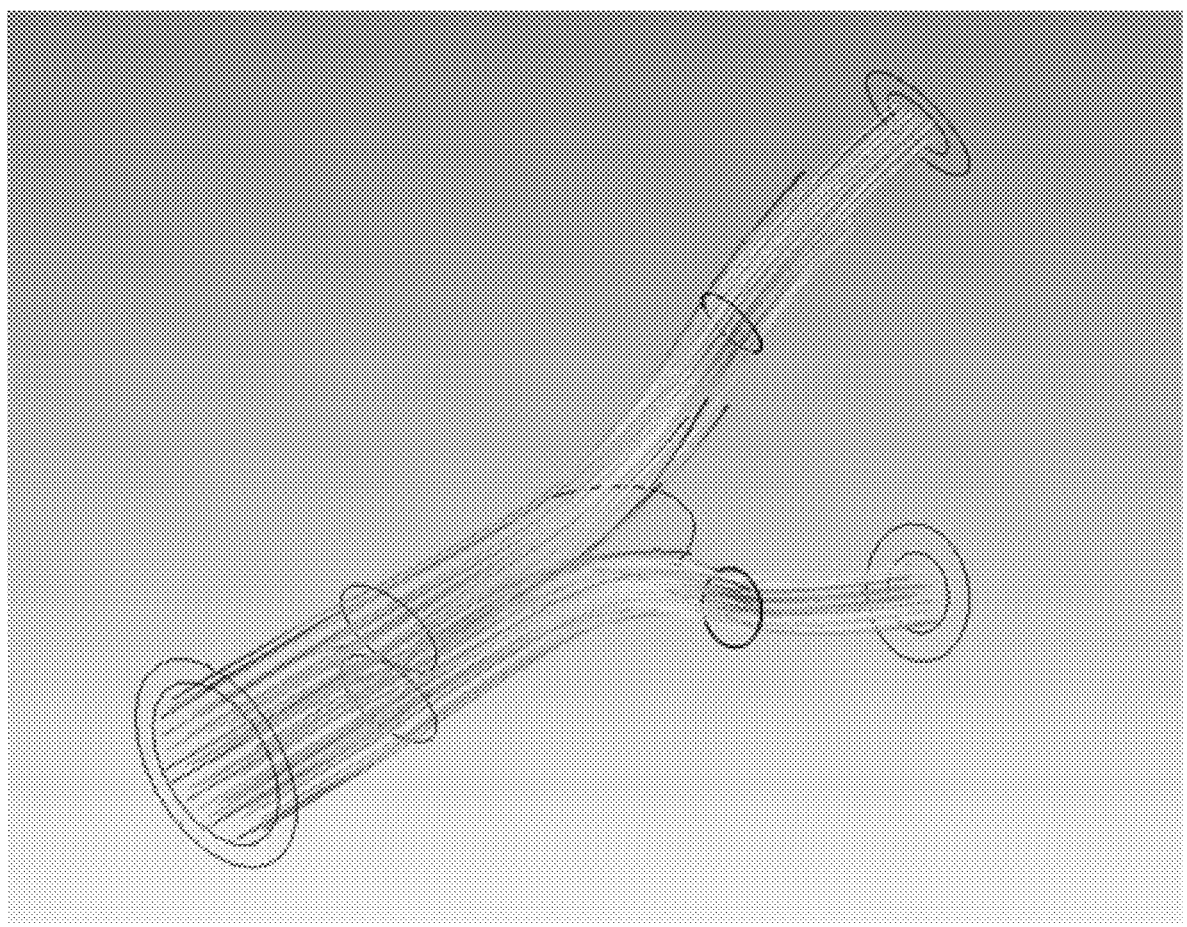
FIG. 12E is a model of the velocity streamlines of the kissing stent aortic bifurcation model.

The kissing stent aortic bifurcation velocity contour plot in FIG. 12B shows a gradual velocity a bit less than what is expected in the distal aorta. This is possibly due to the sudden change in cross-section due to the kissing stent inlet. Using the color velocity scale as a guide, the inlet of the two kissing stents showed a rapid increase in velocity in each stent and even more of a velocity increase at the outlet of each artery. There was also a particularly large radial spread in velocity in the distal iliac vessels. These large jumps in velocity are considered to be suboptimal and can introduce unwanted stress in the aortic bifurcation. In terms of velocity direction, FIG. 12C shows a few velocity disturbances in the kissing stent aortic bifurcation model. Most notably, the disturbance around the entrance of the kissing stents shows stagnation and backflow of the blood. An image of this disturbance can be seen in FIG. 14A. In this figure, blood flow in the distal aorta is impacted by the abrupt surface that the kissing stents create due to the presence of two new inlets with no smooth transition. This results in the collection of flow around the edge of the kissing stent inlets, stagnation at the outer edge of the distal aorta at this location, and backflow to allow flow into each kissing stent inlet.

Figure 14A:
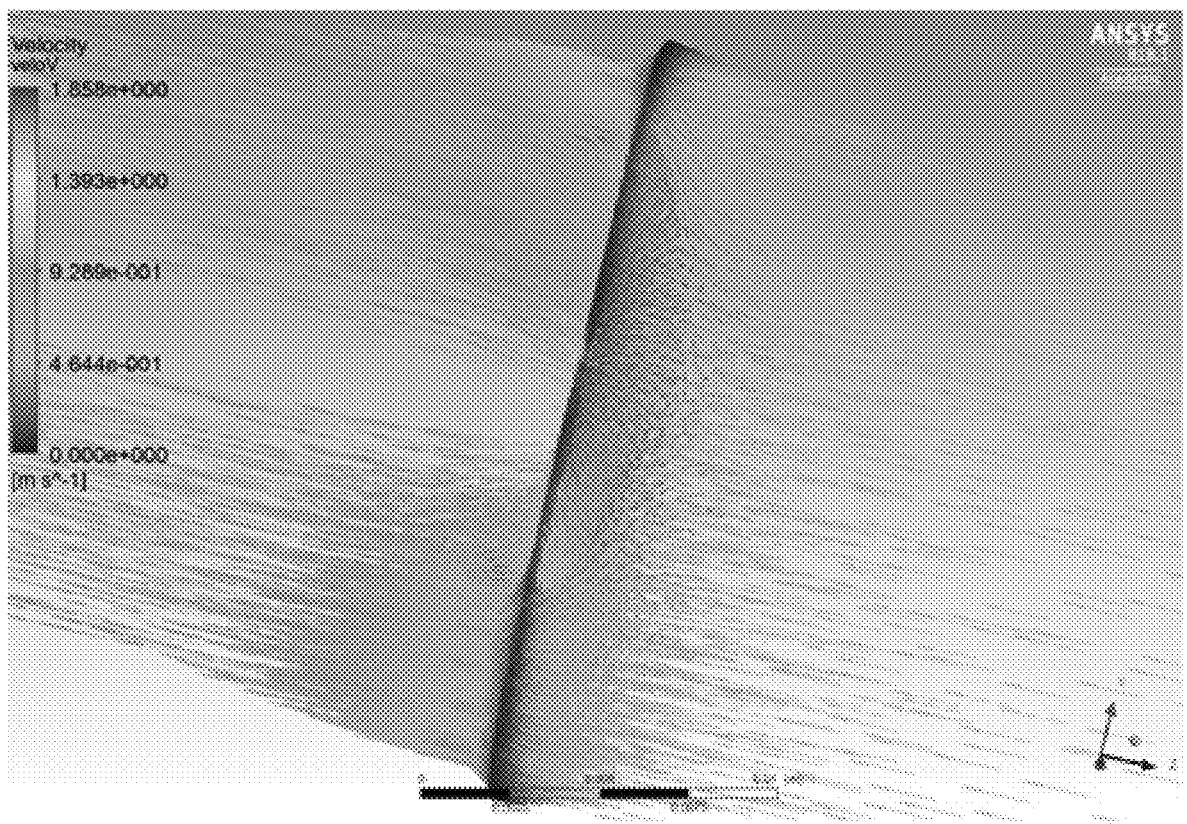
FIG. 14A is a zoomed in model of the velocity vectors of the kissing stent aortic bifurcation model. The image depicts the inlet of the two kissing stents in the distal aorta.

These drawbacks to the kissing stent design are not artifacts of the modeling. The modeling of the kissing stent inlet in the distal aorta if anything attenuated the propensity for such artifacts. Typically, the stents crush and press plaques present up to the vessel walls to create new lumens for blood flow. However, kissing stents typically leave gaps where the two stents touch in the distal aorta. Blood flow in these gaps causes significant thrombus formation in the bifurcation. In the Examples, the plaque was assumed to fill these gaps and form a solid barrier around the two kissing stents. This should attenuate backflow in the model. Even with this attenuation, back flow still occurred, as seen in FIG. 14A. This backflow is a significant disadvantage to treatment using the kissing stent method.

The fenestrated stent model showed a flow field that was free of deleterious features. The gradual velocity in the distal aorta was similar to the healthy aortic bifurcation model and the transition of velocity into the stent was constant. This shows an improved resultant flow at the inlet of the stent. Blood flow was less radially distributed in the common iliac vessels and suitable velocities nearly equivalent to the healthy bifurcation model were observed. This suggests that the fenestrated stent technique is more suitable for treating the aortic bifurcation than the kissing stent technique.

Figure 13C:
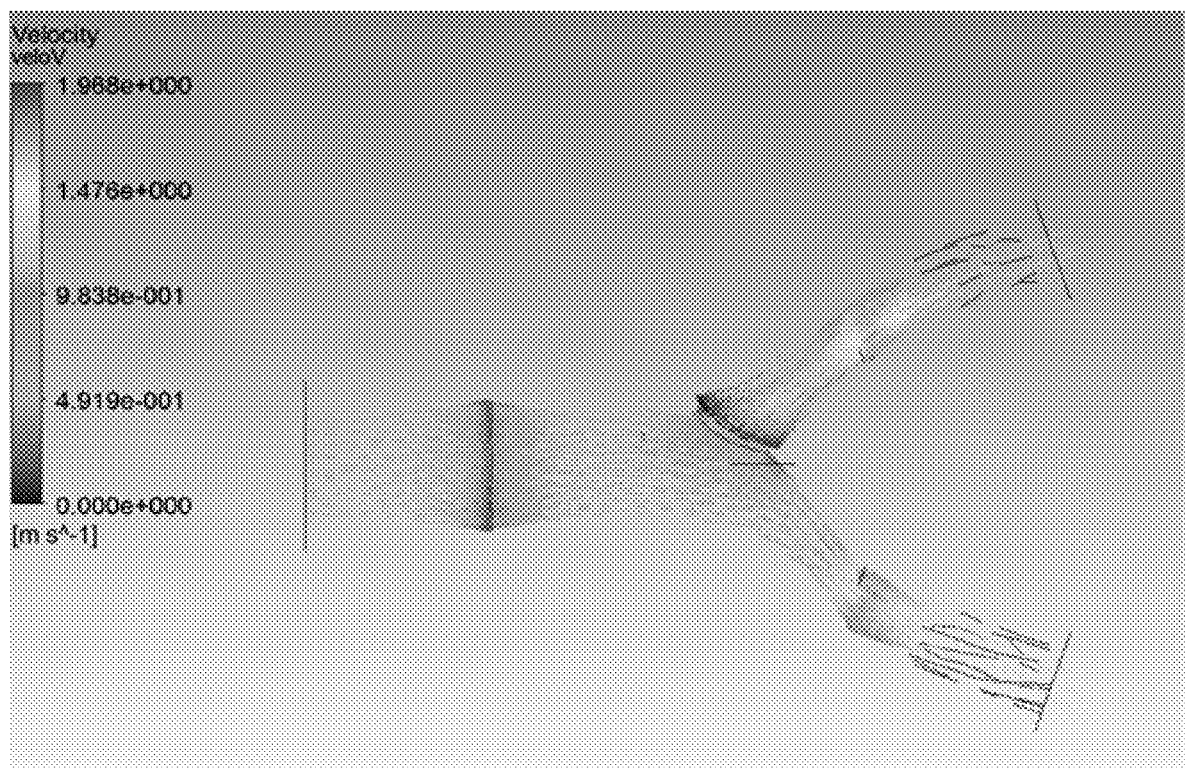
FIG. 13C is a model of the velocity vector map of the fenestrated stent aortic bifurcation model.
Figure 13D:
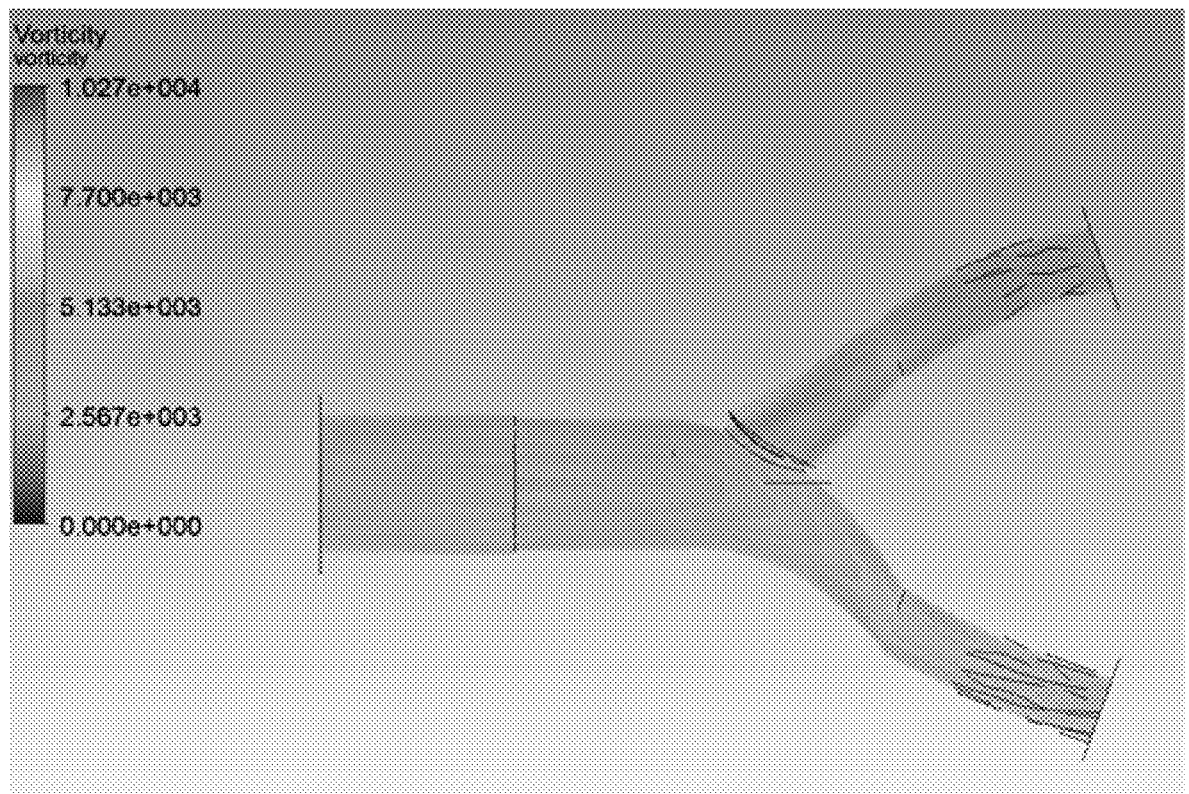
FIG. 13D is a model of the vorticity of the fenestrated stent aortic bifurcation model.
Figure 14B:
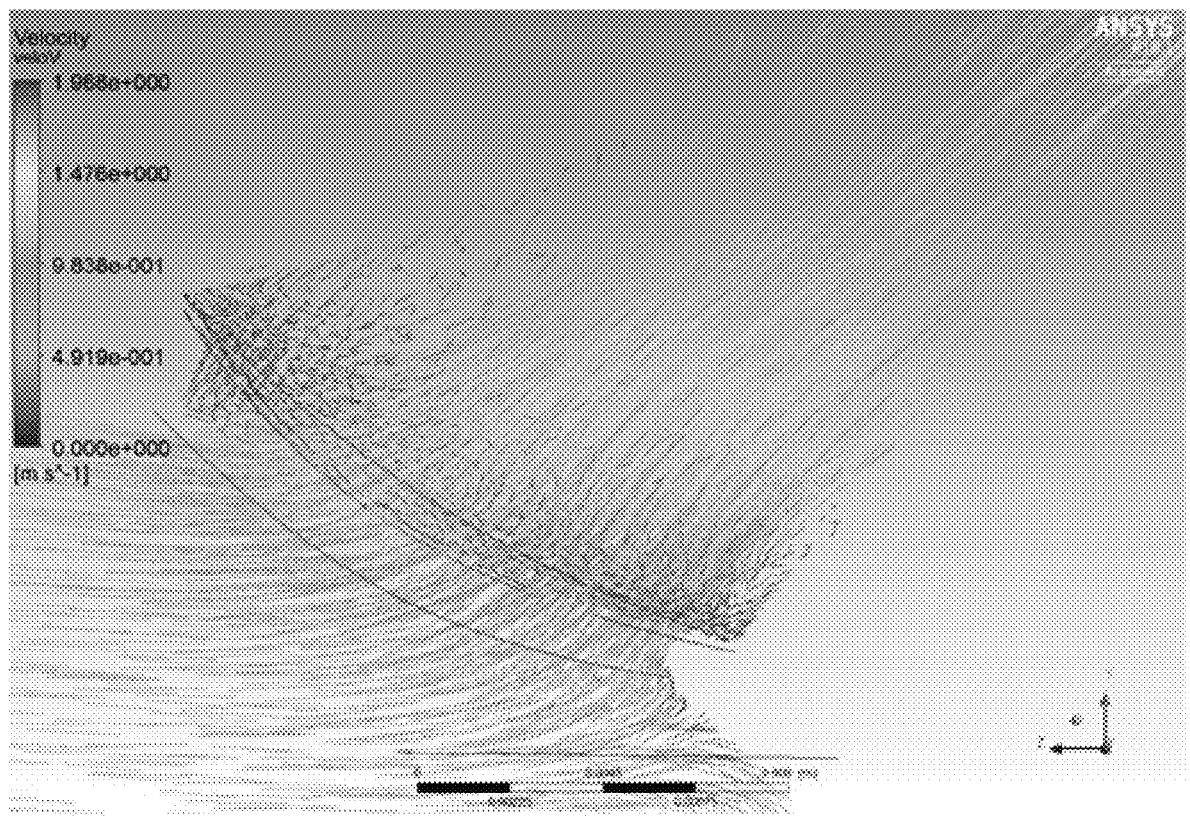
FIG. 14B is a zoomed in model of the velocity vectors of the fenestrated stent aortic bifurcation model. The image depicts the exit of the fenestration into the contralateral common iliac artery.
Figure 15A:
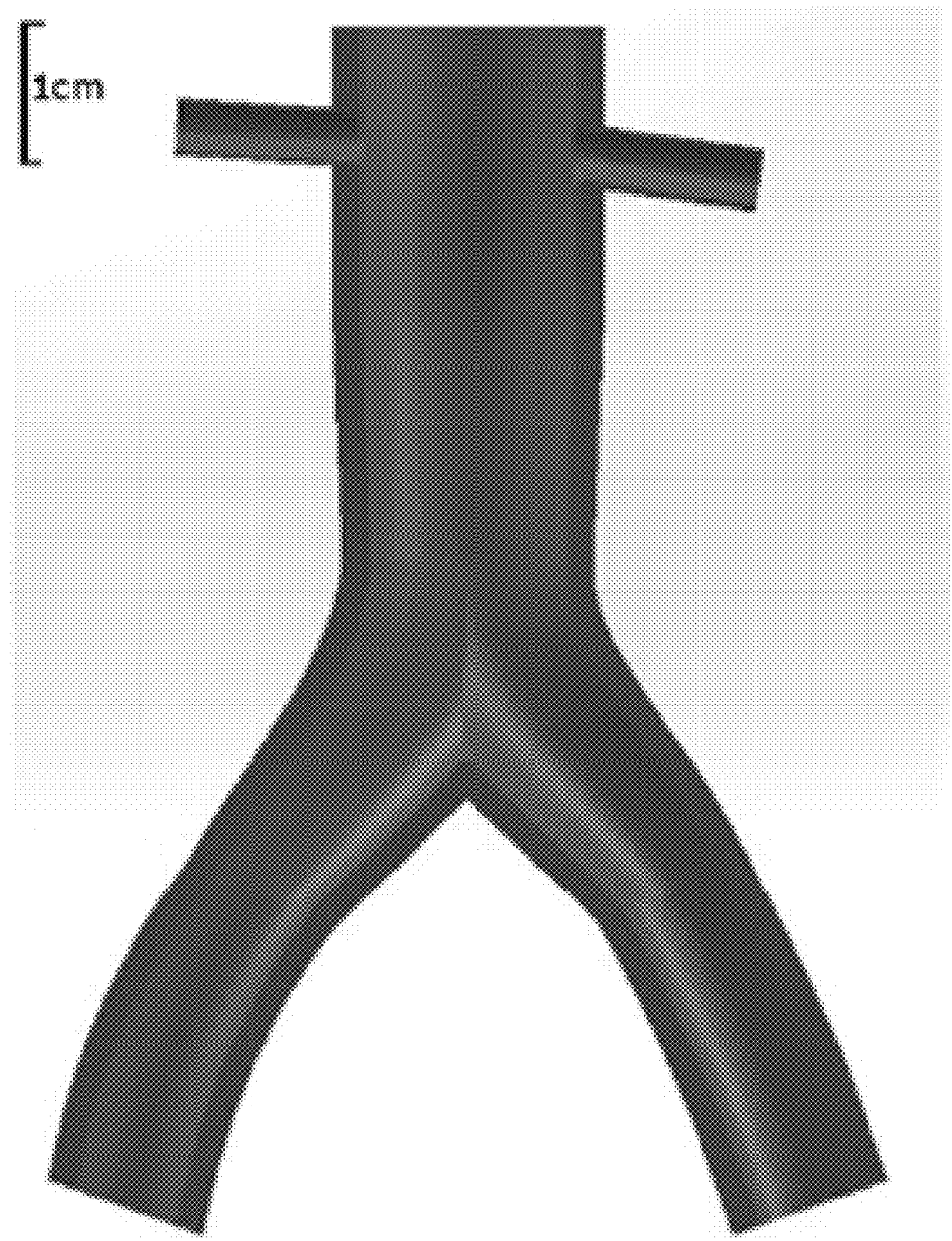
FIG. 15A is a computer generated cross-section of a healthy aortic bifurcation.
Figure 15B:
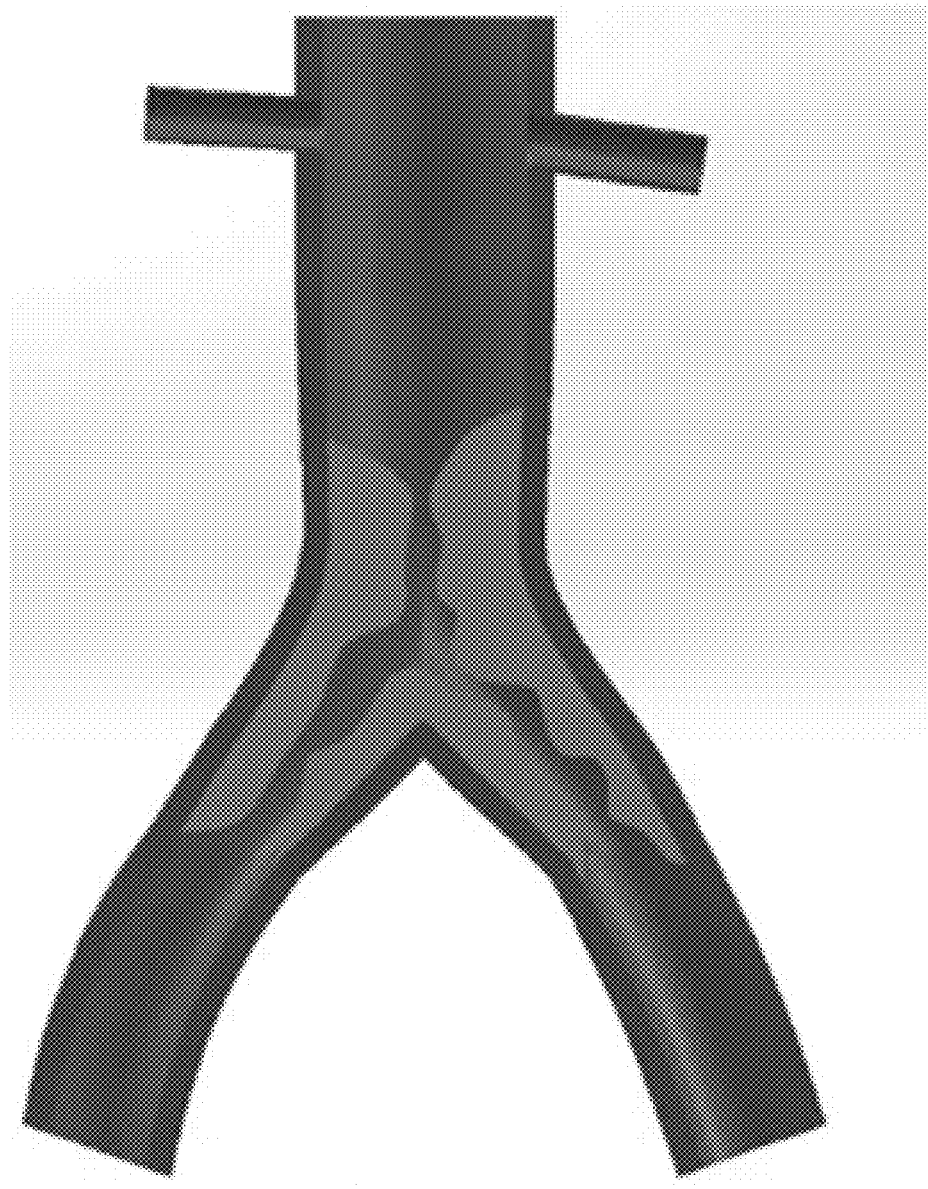
FIG. 15B is a computer generated cross-section of an unhealthy, plaque occluded aortic bifurcation.
Figure 15C:
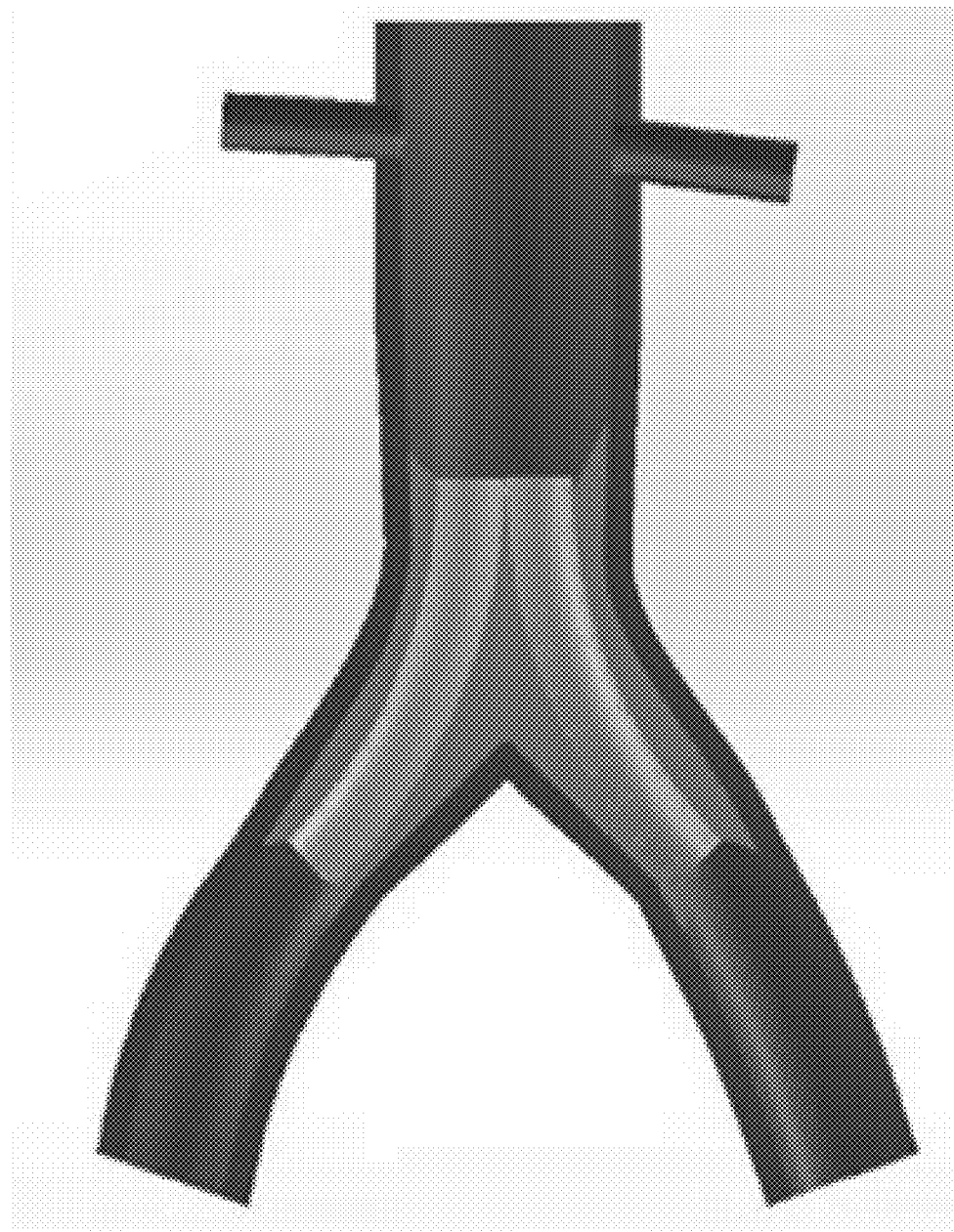
FIG. 15C is a computer generated cross-section of ideally deployed "kissing" stents.
Figure 16:
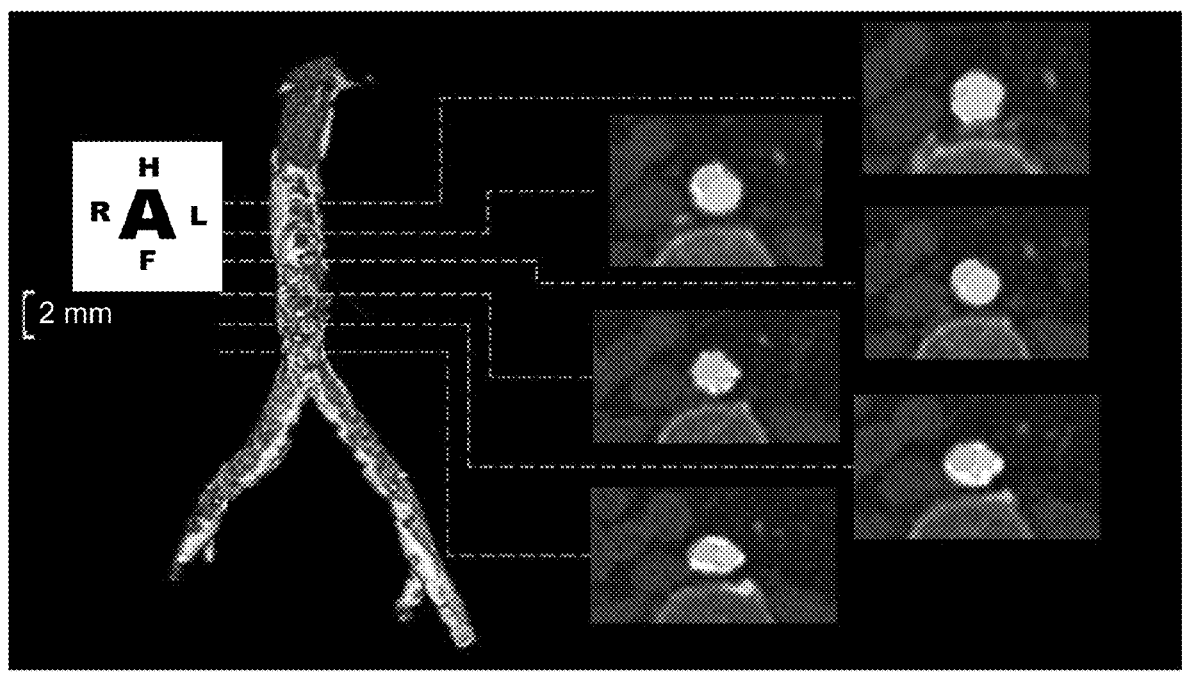
FIG. 16 is a representative MRI of a patient with kissing aortoiliac stents applied, with cross-sections taken at equally spaced intervals within the aorta. Purple and green coloring has been applied to illustrate observed occlusion.
Figure 19A:
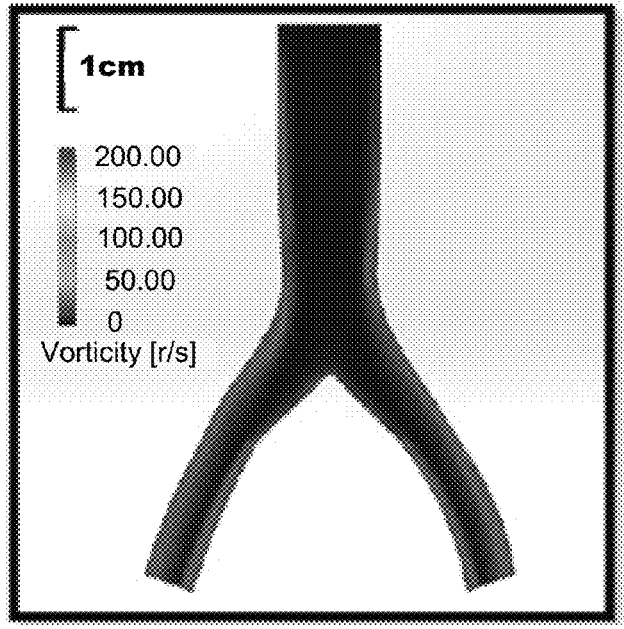
Figure 19B:
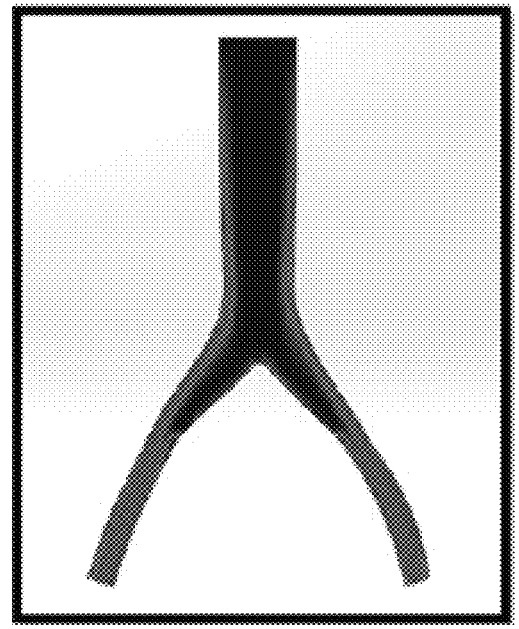
Figure 19C:
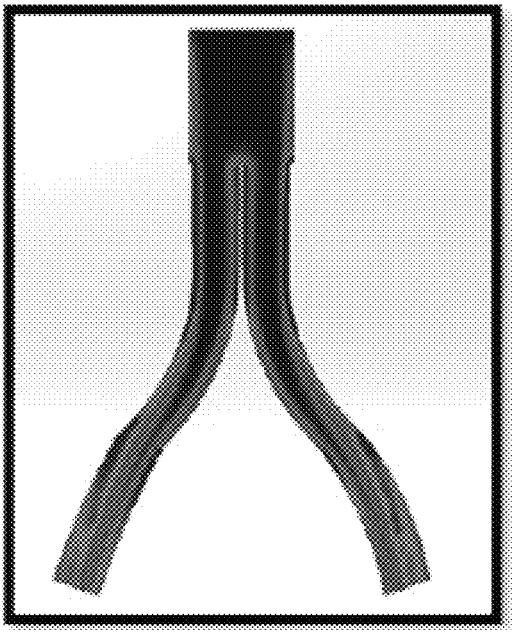
Figure 19D:
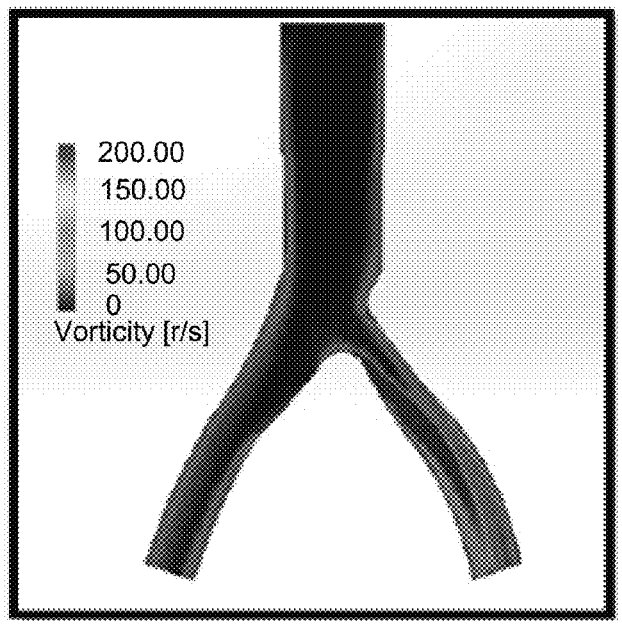

The velocity vector plot of the fenestrated stent model in FIG. 13C shows a large collection of vectors near the lips of the stents. However, no stagnation or backflow was observed. Potential stagnation of blood around the external edges of the fenestration is possible, however, due to a small pocket being created by the complementing common iliac stent. This result can be seen in FIG. 14B.

Figure 13E:
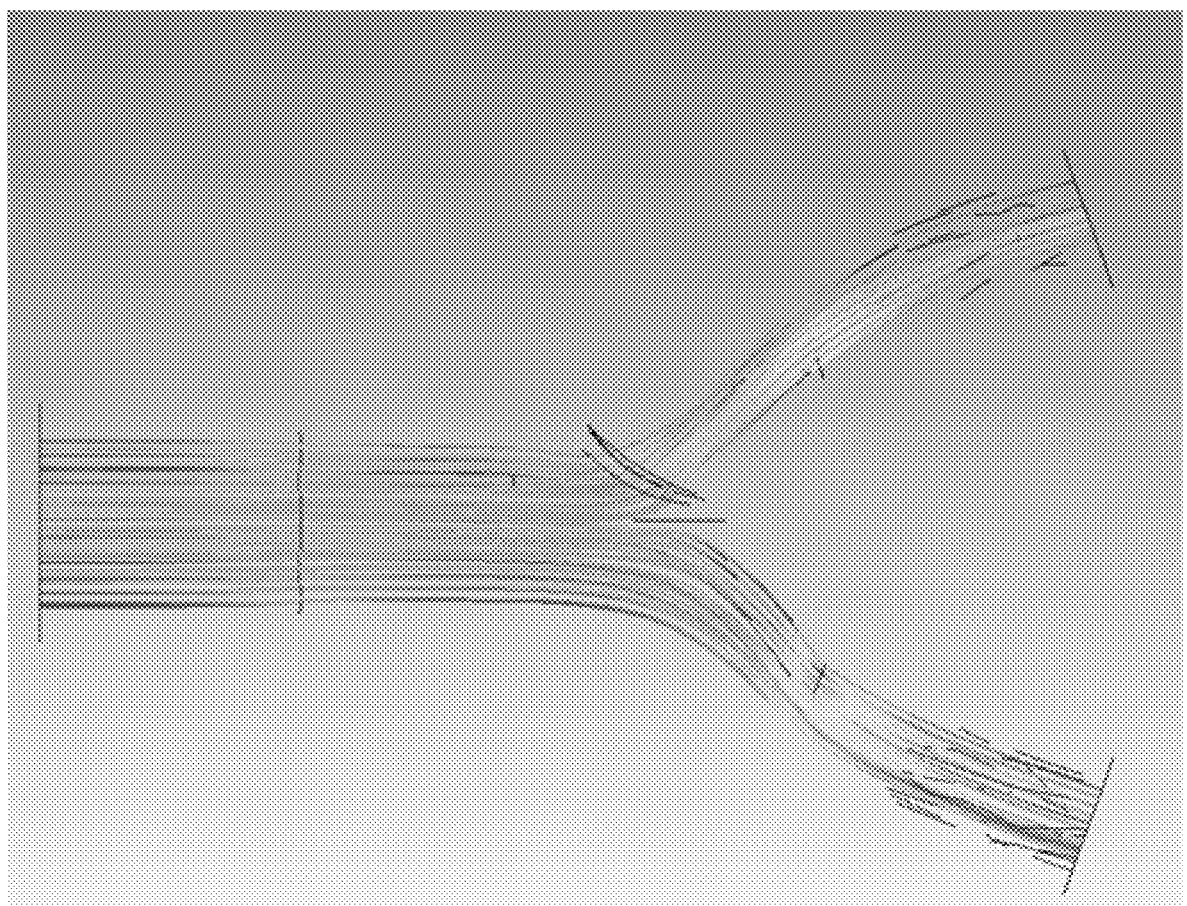
FIG. 13E is a model of the velocity streamlines of the fenestrated stent aortic bifurcation model.

The streamlines of the fenestrated stent aortic bifurcation mode in FIG. 13E show that blood flow was not evenly distributed in this model. A significant portion of the flow can be observed following the fenestrated stent instead of evenly distributing between the stent and the fenestration itself. This flow can be balanced through optimizing the stent geometry.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A fenestrated stent system for placement in the aortic bifurcation, the fenestrated stent system comprising:
    a fenestrated stent having a distal aorta end and a common iliac end, the fenestrated stent comprising a fenestration at a point between the distal aorta end and the common iliac end and at least one radiopaque marker on an outer surface of the fenestrated stent; and
    a common iliac stent having a proximal end and a distal end, the common iliac stent operable for placement through the fenestration of the fenestrated stent and in the contralateral common iliac artery,
    wherein the fenestrated stent is tapered 45% to 80% from the distal aorta end to the common iliac end and the common iliac stent is tapered 5% to 25% from the proximal end to the distal end, and
    wherein the fenestration comprises a radiopaque wireframe on the fenestration border.

2. The fenestrated stent system of claim 1, wherein the fenestrated stent is 8 cm in length.

3. The fenestrated stent system of claim 1, wherein the taper from the distal aorta end to the common iliac end is 50%.

4. The fenestrated stent system of claim 3, wherein the distal aorta end has a diameter of 14 mm and the common iliac end has a diameter of 7 mm.

5. The fenestrated stent system of claim 1, wherein the fenestration has an oval, circular, or triangular shape.

6. The fenestrated stent system of claim 5, wherein the fenestration is oval-shaped and has a size of 10 mm by 8 mm.

7. The fenestrated stent system of claim 1, wherein the fenestrated stent and the common iliac stent are balloon expandable.

8. The fenestrated stent system of claim 1, wherein the at least one radiopaque marker is a series of radiopaque lines oriented perpendicular to one another on the outer surface of the fenestrated stent.

9. The fenestrated stent system of claim 1, wherein the common iliac stent comprises at least one radiopaque marker.

10. A method of treating aortoiliac occlusion disease, comprising:

placing a fenestrated stent at a location in the aortic bifurcation, the fenestrated stent having a distal aorta end and a common iliac end an comprising a fenestration at a point between the distal aorta end and the common iliac end and at least one radiopaque marker on an outer surface of the fenestrated stent, wherein the fenestrated stent is tapered 45% to 80% from the distal aorta end to the common iliac end, and wherein the fenestration comprises a radiopaque wireframe on the fenestration border;

identifying the location of the fenestrated stent;

adjusting the fenestrated stent such that the distal aorta end is in the aorta and the common iliac end is in a common iliac;

identifying the location of the fenestration;

adjusting the fenestrated stent so that the fenestration aligns with the contralateral common iliac;

expanding a balloon to expand the fenestrated stent; and placing a common iliac stent through the fenestration of the fenestrated stent and in the contralateral common iliac artery, wherein the common iliac stent is tapered 5% to 25% from a proximal end to a distal end of the common iliac stent.

11. The method of claim 10, wherein the fenestrated stent is 8 cm in length.

12. The method of claim 10, wherein the taper from the distal aorta end to the common iliac end is 50%.

13. The method of claim 12, wherein the distal aorta end has a diameter of 14 mm and the common iliac end has a diameter of 7 mm.

14. The method of claim 10, wherein the fenestration has an oval, circular, or triangular shape.

15. The method of claim 14, wherein the fenestration is oval-shaped and has a size of 10 mm by 8 mm.

16. The method of claim 10, wherein the at least one radiopaque marker is a series of radiopaque lines oriented perpendicular to one another on the outer surface of the fenestrated stent.

17. The method of claim 10, wherein the common iliac stent comprises at least one radiopaque marker.

* * * * *